(12) United States Patent
Myles et al.

(10) Patent No.: US 7,342,124 B2
(45) Date of Patent: Mar. 11, 2008

(54) SYNTHETIC TECHNIQUES AND INTERMEDIATES FOR POLYHYDROXY DIENYL LACTONES AND MIMICS THEREOF

(75) Inventors: David C. Myles, Kensington, CA (US); Mark Burlingame, Oakland, CA (US); Simon James Shaw, San Francisco, CA (US); Kurt F. Sundermann, Burlingame, CA (US); Brian Scott Freeze, Philadelphia, PA (US); Ignació Brouard Martin, Canary Islands (ES); Tomoyasu Hirose, Tokyo (JP); Amos B. Smith, III, Merion, PA (US)

(73) Assignees: The Trustees Of The University Of Pennsylvania, Philadelphia, PA (US); Kosan Biosciences, Inc., Hayward, CA (US)

( * ) Notice: Subject to any disclaimer, the term of this patent is extended or adjusted under 35 U.S.C. 154(b) by 157 days.

(21) Appl. No.: 10/817,532

(22) Filed: Apr. 2, 2004

(65) Prior Publication Data

US 2005/0049414 A1    Mar. 3, 2005

Related U.S. Application Data

(60) Provisional application No. 60/460,744, filed on Apr. 2, 2003, provisional application No. 60/476,378, filed on Jun. 6, 2003.

(51) Int. Cl.
*C07F 9/02* (2006.01)
*C07C 67/02* (2006.01)
(52) U.S. Cl. .................. 556/404; 560/262; 568/11
(58) Field of Classification Search .......... 568/11; 560/262; 556/404
See application file for complete search history.

(56) References Cited

U.S. PATENT DOCUMENTS

| | | | |
|---|---|---|---|
| 5,010,099 A | 4/1991 | Gunasekera et al. | 514/459 |
| 5,681,847 A | 10/1997 | Longley et al. | 514/459 |
| 5,789,605 A | 8/1998 | Smith, III et al. | 549/370 |
| 6,031,133 A | 2/2000 | Smith, III et al. | 564/170 |
| 6,096,904 A * | 8/2000 | Smith et al. | 549/292 |
| 6,242,616 B1 | 6/2001 | Smith, III et al. | 549/292 |
| 2002/0103387 A1 | 8/2002 | Smith, III et al. | 549/292 |

FOREIGN PATENT DOCUMENTS

WO    WO 03/013502 A1    2/2003

OTHER PUBLICATIONS

Smith et al. Organic Letters, 1999, vol. 1, pp. 1823-1826.*
Harried, S.S., et al., "Total synthesis of (-)-discodermolide: an application of a chelation-controlled alkylation reaction," *J. Org. Chem.*, 1997, 62, 6098-6099.
Hodges, J.C., et al., "Reactions of lithiooxazole," *Am. Chem. Soc.*, 1991, 449-452.
Hung, D.T., et al., "Syntheses of discodermolides useful for investigating microtubule binding and stabilization," *J. Am. Chem. Soc.*, 1996, 118, 11054-11080.
Smith, A.B., III, et al., "Total synthesis of (-)-discodermolide," *J. Am. Chem. Soc.*, 1995, 117, 12011-12012.
Greene, et al., *Protective Groups in Organic Synthesis*, 3rd Ed., John Wiley & Sons, NY, 1999.
Gunasekera, S.P., et al., "Discodermolide: a new bioactive polyhydroxylated lactone from the marine sponge *discodermia dissolute*," *J. Org. Chem.*, 1990, 55, 4912-4915 (original article) (correction published in journal at: *J. Org. Chem.*, 1991, 56, p. 1346).
Hung, D.T., et al., "(+)-discodermolide binds to microtubules in stoichiometric ratio to tubulin dimmers, blocks taxol binding and results in mitotic arrest," *Chem. & Biol.*, 1996, 3, 287-293.
Hung, D.T., et al., "Distinct binding and cellular properties of synthetic (+)- and (-)- discodermolides," *Chem. & Biol.*, 1994, 1, 67-71.
Longley, R.E., et al., "Discodermolide—a new, marine-derived immunosuppressive compound," *Transplantation*, 1991, 52(4), 650-656.
Longley, R.E., et al., "Discodermoldine—a new, marine-derived immunosuppressive compound," *Transplantation*, 1991, 52(4), 656-661.
Longley, R.E., et al., "Immunosuppression by discodermolide," *Ann. N.Y. Acad. Sci.*, 1993, 696, 94-107.
Martello, L.A., et al. "The relationship between taxol and (+)-discodermolide: synthetic analgs and modeling studies," *Chem. & Biol.*, 2001, 8, 843-855.
Nerenberg, J.B., et al., "Total synthesis of the immunosuppressive agent," *J. Am. Chem. Soc.*, 1993, 115, 12621-12622.
Smith, A.B., et al., "A practical improvement, enhancing the large-scale synthesis of (+)-discodermolide: a third-generation approach," *Org. Lett.*, 2003, 5(23), 4405-4408.
ter Haar, E., et al., "Discodermolide, a cytotoxic marine agent that stabilizes microtubules more potently than taxol," *Biochemistry*, 1996, 35, 243-250.

* cited by examiner

*Primary Examiner*—Margaret D. Seaman
*Assistant Examiner*—Niloofar Rahmani
(74) *Attorney, Agent, or Firm*—Woodcock Washburn LLP

(57) ABSTRACT

Synthetic methods and intermediates useful in the preparation of lactone containing compounds such as discodermolide and compounds which mimic the chemical or biological activity of discodermolide are provided.

23 Claims, No Drawings

SYNTHETIC TECHNIQUES AND INTERMEDIATES FOR POLYHYDROXY DIENYL LACTONES AND MIMICS THEREOF

CROSS-REFERENCE TO RELATED APPLICATIONS

This application claims the benefit under 35 USC § 119 (e)(1) of application Ser. No. 60/460,744, filed Apr. 2, 2003 and application Ser. No. 60/476,378, filed Jun. 6, 2003. The disclosure of each of the foregoing is hereby incorporated herein by reference in its entirety.

GOVERNMENT SUPPORT

This invention was made in part with Government support under Grant No. DADM 7-00-1-0404 awarded by U.S. Army. The Government has certain rights in this invention.

FIELD OF THE INVENTION

The present invention relates to lactone-containing compounds and methods of their manufacture. The present invention also relates to phosphonium salt-containing compounds and methods of their manufacture. In certain embodiments, the phosphonium salt-containing compounds and methods of their manufacture and use provide useful intermediates in the synthesis of discodermolide or compounds which mimic the chemical and/or biological activity thereof.

BACKGROUND OF THE INVENTION

In 1990, Gunasekera and co-workers at the Harbor Branch Oceanographic Institute reported the isolation of (+)-discodermolide (1), an architecturally novel metabolite of the marine sponge *Discodermia dissoluta* (0.002% w/w). (See, Gunasekera, et al., *J. Org. Chem.* 1990, 55, 4912. Correction: *J. Org. Chem.* 1991, 56, 1346).

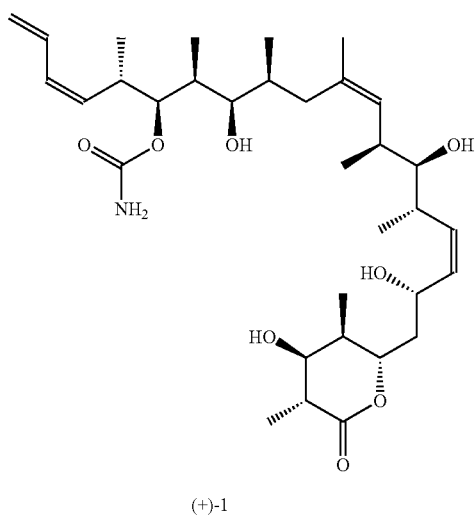

(+)-1

Initial studies revealed that (+)-discodermolide suppresses both the two-way mixed-lymphocyte reaction and the concanavalin A-induced mitogenesis of murine splenocytes in vitro with no associated cytotoxicity. Moreover, (+)-1 suppresses the in vivo graft-vs.-host splenomegaly response induced by injection of parental splenocytes into F1 recipient mice, with potency intermediate between those of cyclosporin A and FK506. (Longley, et al., *Transplantation* 1991, 52, 650; Longley, et al., *Transplantation* 1991, 52, 656; Longley, et al. *Ann. N.Y. Acad. Sci.* 1993, 696, 94). These findings stimulated the recent discovery that (+)-1 arrests cell development at the M phase by binding and stabilizing mitotic spindle microtubules; thus discodermolide resembles taxol in its mode of action, but the microtubule binding affinity of 1 is much higher. (ter Haar, et al., *Biochemistry* 1996, 35, 243; Hung, et al., *Chemi. & Biol.* 1996, 3, 287). These and other results suggest that (+)-discodermolide holds considerable promise as an anti-cancer agent. Due to the scarcity of natural material, complete evaluation of its biological profile has depended almost wholly on (+)-discodermolide's synthetic preparation.

The absolute configuration of discodermolide remained undefined until Schreiber et al. synthesized both antipodes of 1. (Nerenberg, et al. *J. Am. Chem. Soc.* 1993, 115, 12621; Hung, et al., *Chem. & Biol.* 1994, 1, 67). Interestingly, the unnatural (−) antipode also displays significant immunosuppressant activity.

One of the key structural features of discodermolide its $\Delta^{8,9}$-olefinic bond. cis-Selectivity at the $\Delta^{8,9}$-double bond in discodermolide compounds or analogs thereof is highly desirable for chemical or biological activity of these molecules. Martello, L. A., et al., *Chem. Biol.*, 2001, 120, 1. In approaching the synthesis of discodermolide compounds, Smith, et al. (U.S. Pat. No. 6,242,616 B1) employed Wittig chemistry to provide the eventual $\Delta^{8,9}$-double bond of certain discodermolide intermediate compounds bearing an acid labile hydroxyl protecting group at C-11. Under certain reaction conditions using phosphonium salt intermediates with bulky trialkylsilyl acid labile C-11 hydroxyl protecting groups, the reaction provided cis/trans ratios of about 20 at the $\Delta^{8,9}$-double bond in good yield. Unfortunately, preparation of the desired Wittig precursor phosphonium salts to discodermolide compounds having these specified C-11 protecting groups has the drawback of requiring the use of very high pressure (as great as 12 kbar or above). Reaction rates in some instances are very slow and, as such, the reactions require extended reaction times (as long as 10-14 days). Use of these very high pressure process conditions has the further drawback of requiring specialized reactors and handling equipment. In the absence of these extreme pressure conditions, undesirable amounts of cyclized by-products are formed (Scheme 1). Attempted formation of certain phosphonium salts under more convenient ambient pressure conditions led to HI-catalyzed decomposition and increased levels of cyclized by-products. Smith, et al., *Org. Lett.* (2003), 5(23), 4405-4408.

Scheme 1

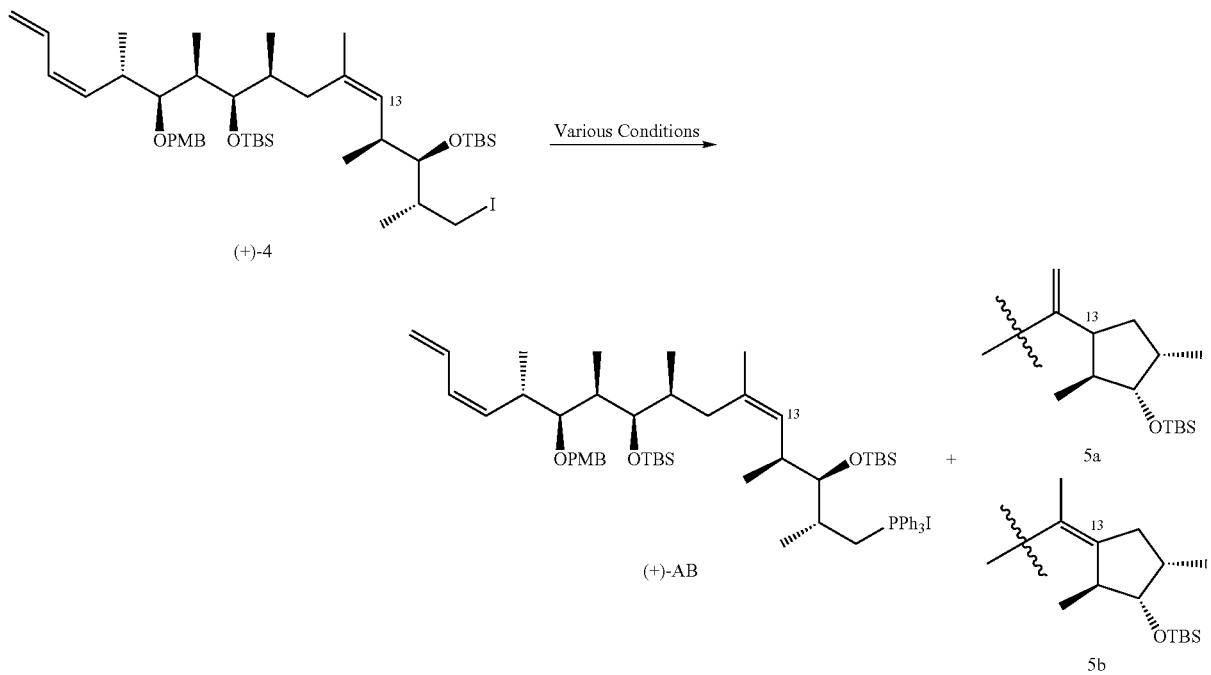

There is therefore a need for improved synthetic methods which provide high yield and high selectivity, and at a relatively high rate of reaction, using better, more convenient and/or less expensive process methodology than many processes known heretofore for the preparation of polyhydroxy, dienyl lactones such as the discodermolides and their synthetic intermediates, as well as a need for compounds having similar chemical and/or biological activity. The present invention is directed to these and other important ends.

SUMMARY OF THE INVENTION

In some embodiments the present invention is generally directed to lactone-containing compounds and methods of their manufacture. In other embodiments the present invention is generally directed to phosphonium salt-containing compounds and methods of their manufacture.

In certain embodiments the invention is directed to processes for preparing a compound of formula I:

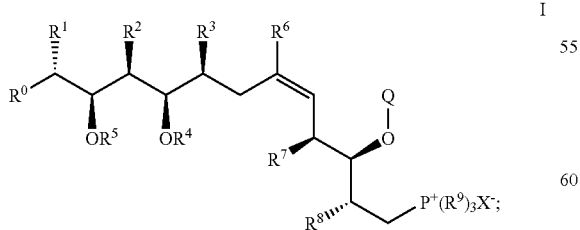

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;

$R^1$, $R^2$, $R^3$, $R^6$, $R^7$ and $R^8$ are independently H or $C_{1-10}$ alkyl;

$R^4$ is an acid labile hydroxyl protecting group;

$R^5$ is an oxidatively labile hydroxyl protecting group;

each $R^9$ is independently $C_{6-14}$ aryl;

Q is H or an acid labile hydroxyl protecting group wherein the hydroxyl protecting group has a mass of 135 Daltons or less and is unbranched at the atom bonded to the oxygen of the hydroxyl group being protected; and X is halogen;

comprising contacting a compound of formula II:

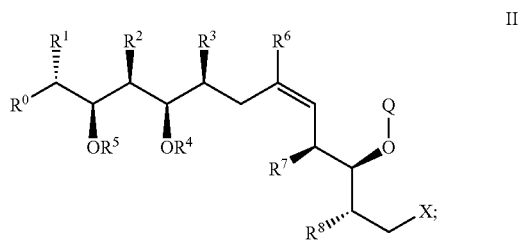

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;

$R^1$, $R^2$, $R^3$, $R^6$, $R^7$ and $R^8$ are independently H or $C_{1-10}$ alkyl;

$R^4$ is an acid labile hydroxyl protecting group;

$R^5$ is an oxidatively labile hydroxyl protecting group;

Q is H or an acid labile hydroxyl protecting group wherein the hydroxyl protecting group has a mass of 135

Daltons or less and is unbranched at the atom bonded to the oxygen of the hydroxyl group being protected; and X is halogen;

at a pressure of less than about 10,000 psi with a phosphine of formula P(R$^9$)$_3$, wherein each R$^9$ is independently C$_{6-14}$ aryl, for a time and under conditions sufficient to prepare the compound of formula I.

In other embodiments the invention is directed to compounds of the formula I:

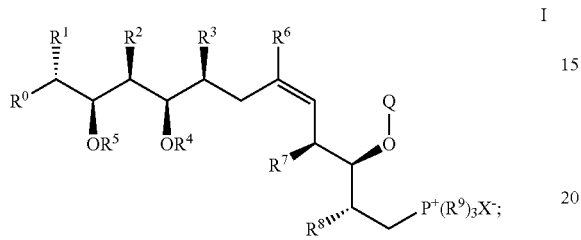

I wherein:
R$^0$ is C$_{1-6}$ alkyl, C$_{2-6}$ alkenyl, C$_{2-6}$ alkynyl, (CH$_2$)$_r$(C$_{3-6}$ cycloalkyl), (CH$_2$)$_r$(aryl) or (CH$_2$)$_r$(heterocycle), wherein r is selected from 0, 1, 2, 3, and 4;
R$^1$, R$^2$, R$^3$, R$^6$, R$^7$ and R$^8$ are independently H or C$_{1-10}$ alkyl;
R$^4$ is an acid labile hydroxyl protecting group;
R$^5$ is an oxidatively labile hydroxyl protecting group;
each R$^9$ is independently C$_{6-14}$ aryl;
Q is H or an acid labile hydroxyl protecting group wherein the hydroxyl protecting group has a mass of 135 Daltons or less and is unbranched at the atom bonded to the oxygen of the hydroxyl group being protected; and
X is halogen.

In yet other embodiments, the invention is directed to processes for preparing compounds of formula IIIa:

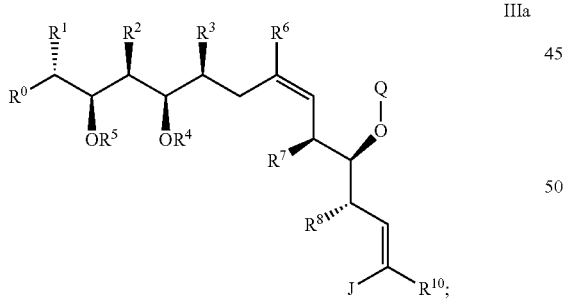

IIIa wherein:
R$^0$ is C$_{1-6}$ alkyl, C$_{2-6}$ alkenyl, C$_{2-6}$ alkynyl, (CH$_2$)$_r$(C$_{3-6}$ cycloalkyl), (CH$_2$)$_r$(aryl) or (CH$_2$)$_r$(heterocycle), wherein r is selected from 0, 1, 2, 3, and 4;
R$_1$, R$^2$, R$^3$, R$^6$, R$^7$ and R$^8$ are independently H or C$_{1-10}$ alkyl;
R$^4$ is an acid labile hydroxyl protecting group;
R$^5$ is an oxidatively labile hydroxyl protecting group;
R$^{10}$ is H or C$_1$-C$_6$ alkyl;
Q is H or an acid labile hydroxyl protecting group wherein the hydroxyl protecting group has a mass of 135

Daltons or less and is unbranched at the atom bonded to the oxygen of the hydroxyl group being protected; and J is:

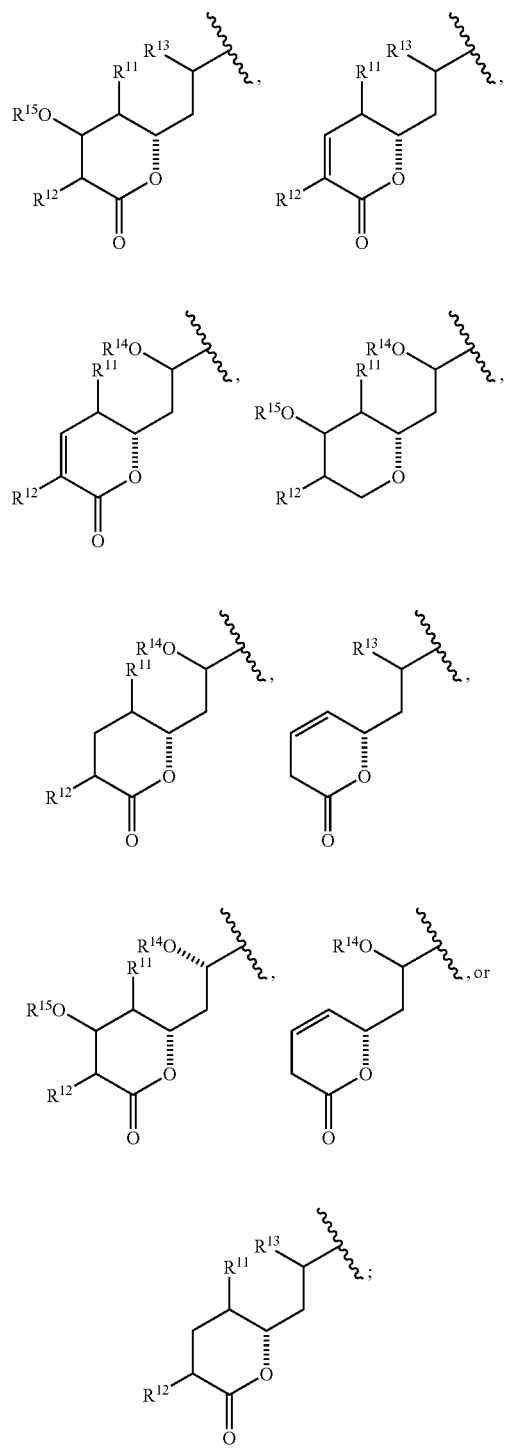

wherein:
R$^{11}$, R$^{12}$ and R$^{13}$ are each independently H or C$_1$-C$_{10}$ alkyl; and
R$^{14}$ and R$^{15}$ are each independently H or an acid labile hydroxyl protecting group;

comprising contacting a compound of formula I:

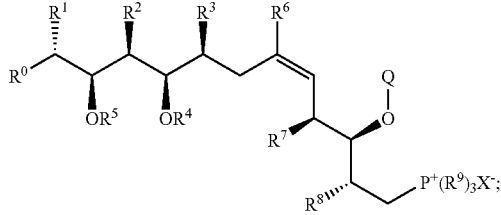

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;

$R^1$, $R^2$, $R^3$, $R^6$, $R^7$ and $R^8$ are independently H or $C_{1-10}$ alkyl;

$R^4$ is an acid labile hydroxyl protecting group;

$R^5$ is an oxidatively labile hydroxyl protecting group;

Q is H or an acid labile hydroxyl protecting group wherein the hydroxyl protecting group has a mass of 135 Daltons or less and is unbranched at the atom bonded to the oxygen of the hydroxyl group being protected;

each $R^9$ is independently $C_{6-14}$ aryl; and

X is halogen;

with a compound of formula J-C(=O)$R^{10}$;

wherein:
$R^{10}$ is H or $C_1$-$C_6$ alkyl; and

J is:

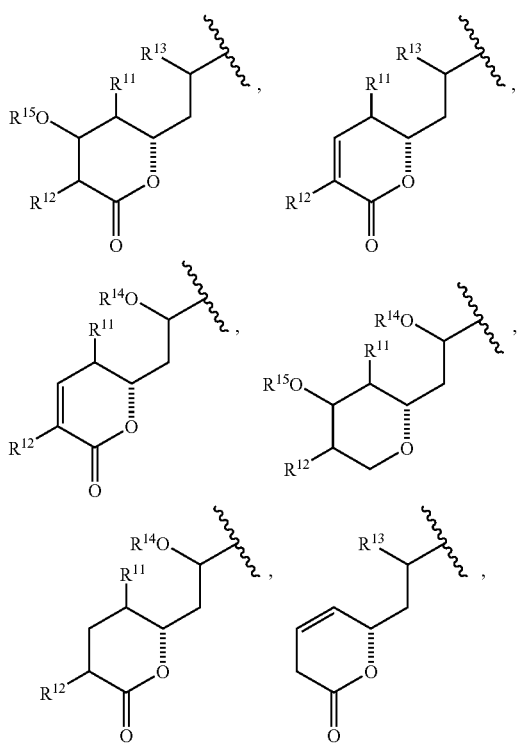

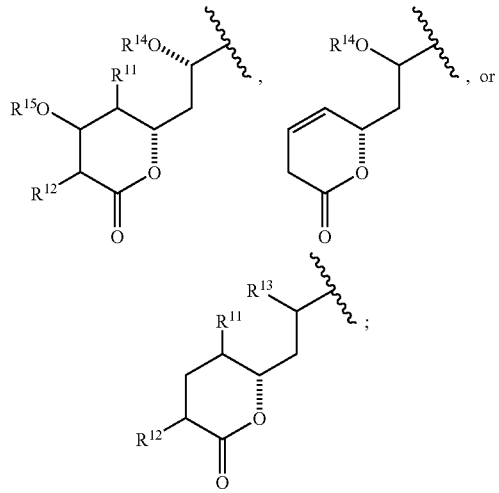

wherein:
$R^{11}$, $R^{12}$ and $R^{13}$ are each independently H or $C_1$-$C_{10}$ alkyl; and $R^{14}$ and $R^{15}$ are each independently H or an acid labile hydroxyl protecting group;

in the presence of a base for a time and under conditions sufficient to prepare the compound of formula IIIa.

DETAILED DESCRIPTION OF THE ILLUSTRATIVE EMBODIMENTS

As employed above and throughout the disclosure, the following terms, unless otherwise indicated, shall be understood to have the following meanings.

As used herein, the term "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 10 carbon atoms being preferred. In other embodiments, hydrocarbons having from about 1 to about 6 carbon atoms, or hydrocarbons having from about 1 to about 3 carbon atoms are preferred. Alkyl groups include, but are not limited to, methyl, ethyl, n-propyl, isopropyl, n-butyl, isobutyl, sec-butyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, the term "alkenyl" refers to an alkyl group having from about 2 to about 10 carbon atoms and one or more double bonds (and all combinations and subcombinations of ranges and specific numbers of carbon atoms therein), with from about 2 to about 6 carbon atoms being preferred, wherein alkyl is as previously defined. Alkenyl groups can be optionally substituted.

As used herein, the term "alkynyl" refers to an alkyl group having from about 2 to about 10 carbon atoms and one or more triple bonds (and all combinations and subcombinations of ranges and specific numbers of carbon atoms therein), with from about 2 to about 6 carbon atoms being preferred, wherein alkyl is as previously defined. Alkynyl groups can be optionally substituted.

As used herein, the term "halo" or "halogen" refers to a fluoro, chloro, bromo, or iodo moiety attached to a compound of the invention.

As used herein, the term "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 14 carbons being preferred. Non-limiting examples include, for example, phenyl, naphthyl, anthracenyl, and phenanthrenyl.

As used herein, the term "cycloalkyl" refers to an optionally substituted, alkyl group having one or more rings in their structures having from about 3 to about 21 carbon atoms (and all combinations and subcombinations of ranges and specific numbers of carbon atoms therein), with from about 3 to about 10 carbon atoms being preferred; more preferably from about 3 to about 6 carbon atoms. Multi-ring structures may be bridged, spiro or fused ring structures. Groups include, but are not limited to, cyclopropyl, cyclobutyl, cyclopentyl, cyclohexyl, cycloheptyl, cyclooctyl, cyclodecyl, cyclododecyl, 2-[4-isopropyl-1-methyl-7-oxa-bicyclo[2.2.1]heptanyl], 2-[1,2,3,4-tetrahydro-naphthalenyl], and adamantyl.

"Heterocycle", "heterocyclic ring", "heterocycle" or "heterocycloalkyl" as those terms are used herein, are intended to mean an optionally substituted stable monocyclic, bicyclic or tricyclic ring system having from about 3 to about 25, preferably 4 to about 15 ring atoms, which is saturated, partially unsaturated or unsaturated (aromatic), and which consists of carbon atoms and from 1 to 3 heteroatoms in at least one of the rings within the ring system independently selected from the group consisting of N, O and S. Thus, the term heterocycle includes aromatic and non-aromatic groups. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Heterocycle includes aromatic heterocyclic systems, herein referred to as "heteroaryl" which consists of carbon atoms and from 1 to 3 heteroatoms per ring independently selected from the group consisting of N, O and S. It is preferred that the total number of S and O atoms in the aromatic heterocycle is not more than 1. Preferably, the heterocycles of the present invention are stable 5- to 10-membered monoi or bicyclic heterocyclic rings, which may be aromatic or non-aromatic.

Examples of heterocycles include, but are not limited to, 2-pyrrolidonyl, 2H-pyrrolyl, 6H-1,2,5-thiadiazinyl, azepinyl, dioxanyl, 1,3-dioxolanyl, 2H,6H-1,5,2-dithiazinyl, furanyl, furazanyl, imidazolidinyl, imidazolinyl, imidazolyl, indolyl, isoxazolyl, isoxazolinyl, isothiazolyl, isothiazolidinyl, morpholinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxetanyl, 2-oxopiperazinyl, 2-oxopiperidinyl, 2-oxo pyrrolidinyl, 2-oxazepinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridinyl, pyridyl, N-oxopyridyl, pyrimidinyl, pyrrolidinyl, pyrrolinyl, pyrrolyl, tetrahydro-1,1-dioxo-thienyl, tetrahydrofuranyl, tetrahydropyranyl, tetrahydrothiopyranyl, tetrahydrothiopyranyl sulfone, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thiazolidinyl, thienyl, thienothiazolyl, thienooxazolyl, thienoimidazolyl, thietanyl, thiiranyl, thiomorpholinyl, thiomorpholinyl sulfoxide, thiomorpholinyl sulfone, thiophenyl, triazinyl, 1,2,3-triazolyl, 1,2,4-triazolyl, 1,2,5-triazolyl, and 1,3,4-triazolyl. Preferred heterocycles include, but are not limited to, pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, and the like. Also included are fused ring and spiro compounds containing, for example, the above heterocycles.

As used herein, the term "aralkyl" refers to alkyl radicals bearing an aryl substituent and have from about 6 to about 50 carbon atoms (and all combinations and subcombinations of ranges and specific numbers of carbon atoms therein), with from about 6 to about 10 carbon atoms being preferred. Aralkyl groups can be optionally substituted. Non-limiting examples include, for example, benzyl, diphenylmethyl, triphenylmethyl, phenylethyl, and diphenylethyl.

As used herein, the term "heteroaralkyl" refers to an optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methyl-cyclopentanyl.

As used herein, the term "spiroalkyl" or "spiro" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Exemplary spiroalkyl groups taken together with its parent group include, but are not limited to, 1-(1-methyl-cyclopropyl)-propan-2-one, 2-(1-phenoxy-cyclopropyl)-ethylamine, and 1-methyl-spiro[4.7]dodecane.

As used herein, "cycloalkylalkyl" refers to an optionally substituted alkyl radical having one or more cycloalkyl substituents, wherein cycloalkyl and alkyl are as previously defined. In some preferred embodiments, the alkyl moieties of the cycloalkylalkyl groups have from about 1 to about 4 carbon atoms. Exemplary cycloalkylalkyl groups include, but are not limited to, cyclohexylmethyl, 4-[4-methyl-decahydronaphthalenyl]-pentyl, 3-[trans-2,3-dimethylcyclooctyl]-propyl, and cyclopentylethyl.

As used herein, the term "stereoisomers" refers to compounds that have identical chemical constitution, but differ as regards the arrangement of the atoms or groups in space.

Where a group is characterized as being optionally substituted, such group may have one or more independently selected substituents, preferably one to five in number, more preferably one or two in number. It is understood that substituents and substitution patterns can be selected by one of ordinary skill in the art to provide compounds that are chemically stable and that can be synthesized by techniques known in the art as well as the methods set forth herein. Examples of suitable substituents include alkyl, alkenyl, alkynyl, aryl, halo, trifluoromethoxy, trifluoromethyl, hydroxy, alkoxy, cycloalkyloxy, heterocyclooxy, alkanoyl, alkanoyloxy, amino, alkylamino, quaternary ammonium, aralkylamino, cycloalkylamino, heterocycloamino, dialkylamino, alkanoylamino, thio, alkylthio, cycloalkylthio, heterocyclothio, ureido, nitro, cyano, carboxy, carboxyalkyl, carbamyl, alkoxycarbonyl, alkylthiono, arylthiono, alkylsulfonyl, sulfonamindo, aryloxy, and the like, in addition to those specified herein. The substituent may be further substituted, for example, by halo, hydroxy, alkyl, alkoxy; aryl, substituted aryl, substituted alkyl, substituted aralkyl, and the like.

As used herein, the term "oxidatively labile hydroxyl protecting group" means those hydroxyl protecting groups removable by an oxidizing agent such as 2,3-dichloro-5,6-dicyano-1,4-benzoquinone ("DDQ"). A non-limiting example of an oxidatively labile hydroxyl protecting group is a p-methoxybenzyl ("PMB" or "MPM") ether group.

As used herein, the term "acid labile hydroxyl protecting group" means an oxygen-bound group that can be removed upon exposure to an acid. Specific examples include, but are not limited to, BOM, acetyl, MOM, MEM, SEM, TBS, triethylsilyl, t-butyldiphenylsilyl, triisopropylsilyl, allyl and tetrahydropyranyl groups.

Many examples of acid labile hydroxyl protecting groups, oxidatively labile hydroxyl protecting groups, and suitable protecting groups Q can be found in Greene and Wuts, *"Protective Groups in Organic Synthesis"*, 3rd edition, pp. 17-245 (John Wiley & Sons, New York, 1999) ("Greene"), along with teachings regarding their manner of use. The disclosure of Greene is incorporated herein by reference.

In some embodiments it is preferable to preserve the chemical distinctiveness between acid labile hydroxyl protecting groups $R^4$, $R^{14}$, $R^{15}$ and Q and oxidatively labile protecting groups $R^5$. Preferably, therefore in some embodiments, the acid labile hydroxyl protecting groups should not be oxidatively labile, and vice-versa.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As used herein, the term "stereoisomers" refers to compounds that have identical chemical constitution, but differ as regards the arrangement of the atoms or groups in space.

Unless particular stereoisomers are specifically indicated (e.g., by a bolded or dashed bond at a relevant stereocenter in a structural formula), all stereoisomers are included within the scope of the invention, as pure compounds as well as mixtures thereof. Compounds employed in the present methods may contain one or more asymmetrically substituted carbon atoms, and may be isolated in optically active or racemic forms. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers. Polymorphic crystalline forms and solvates are also encompassed within the scope of this invention.

As used herein, the term "contacting" refers to the bringing together of compounds to within distances that allow for intermolecular interactions and chemical transformations accompanying such interactions. Often, contacting compounds are in solution phase.

When any variable occurs, more than one time in any constituent or in any formula, its definition in each occurrence is independent of its definition at every other occurrence. Combinations of substituents and/or variable are permissible only if such combinations result in stable compounds.

In certain embodiments directed to a process for preparing compounds of formula I, the present invention provides high yield and high selectivity, and at an increased rate of reaction, using better, more convenient and/or less expensive process methodology than many processes known heretofore for the preparation of synthetic intermediates used in the manufacture of polyhydroxy, dienyl lactones such as the discodermolides. It has been found that the extremely high reaction pressures required in known phosphonium salt forming reactions may be dramatically reduced through judicious choice of protecting groups for the eventual C-11 hydroxyl located adjacent to the introduced phosphonium salt. Surprisingly the rate of reaction is also increased leading to decreased reaction times and more efficient use of equipment. As a direct consequence of reducing reaction pressures, simpler, less costly equipment may be utilized. Even more surprisingly, the levels of decomposition and cyclized by-products are reduced as compared to other reactions employing ambient to moderate reaction pressures.

The compounds of formula I thus provided may be further employed to provide discodermolide compound precursors of formula IIIa. cis-Selectivity at the $\Delta^{8,9}$-double bond in discodermolide and its analogs is important for biological or chemical activity (supra). Prior art Wittig olefination processes developed for more bulky C-11 trialkylsilyl protected Wittig salts (Smith et al. U.S. Pat. No. 6,242,616 B1, "Smith") led to much lower cis/trans olefin ratios in formula IIIa compounds where the trialkylsilyl protecting group was replaced by Q. Substantially higher cis/trans ratios were realized in reactions of C-11 Q-protected Wittig salts under present invention process conditions. Further, the cis/trans ratios provided under present invention process conditions compare favorably with the ratios obtained using the more bulky trialkylsilyl Wittig salts under prior art conditions. Moreover, were the formula I compounds of the present invention to be subsequently used in prior art Wittig olefination processes ("Smith"), present process advantages attributable to the Wittig salt formation step, such as more effective use of process equipment, the use of more convenient, simpler, less costly equipment or reduced inefficiencies in the utilization of costly intermediates, and the like, would be negated due to reductions in cis/trans selectivity for formula IIIa compounds in the prior art olefination step. Consequently, present invention process advantages attributable to Wittig salt formation such as more effective use of process equipment, the use of more convenient, simpler, less costly equipment or reduced inefficiencies in the utilization of costly intermediates, and the like are not negated through reaction inefficiencies of subsequent steps using formula IIIA compounds in prior art processes. When the processes and compounds herein disclosed are utilized within known multi-step syntheses to discodermolide compounds, many advantages may be realized, including increased overall yields, higher overall selectivities, increased reaction rates, more effective use of process equipment, the use of more convenient, simpler, less costly equipment or reduced inefficiencies in the utilization of costly intermediates, and the like. These in turn may lead to lower cost final products and more rapid discovery of additional target compounds with enhanced chemical and/or biological properties.

In certain embodiments the invention is directed to processes for preparing a compound of formula I:

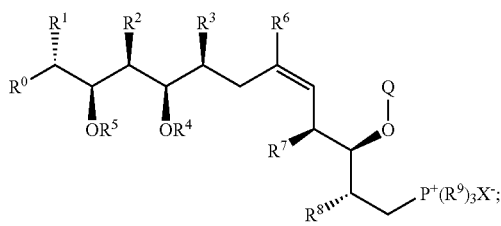

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;
$R^1$, $R^2$, $R^3$, $R^6$, $R^7$ and $R^8$ are independently H or $C_{1-10}$ alkyl;
$R^4$ is an acid labile hydroxyl protecting group;
$R^5$ is an oxidatively labile hydroxyl protecting group;
each $R^9$ is independently $C_{6-14}$ aryl;
Q is H or an acid labile hydroxyl protecting group wherein the hydroxyl protecting group has a mass of 135 Daltons or less and is unbranched at the atom bonded to the oxygen of the hydroxyl group being protected; and
X is halogen;

comprising contacting a compound of formula II:

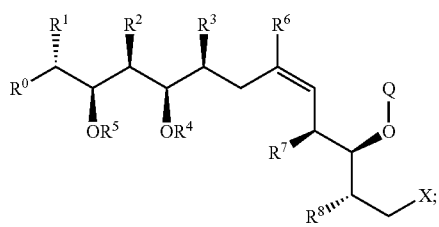

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;
$R^1$, $R^2$, $R^3$, $R^6$, $R^7$ and $R^8$ are independently H or $C_{1-10}$ alkyl;
$R^4$ is an acid labile hydroxyl protecting group;
$R^5$ is an oxidatively labile hydroxyl protecting group;
Q is H or an acid labile hydroxyl protecting group wherein the hydroxyl protecting group has a mass of 135 Daltons or less and is unbranched at the atom bonded to the oxygen of the hydroxyl group being protected; and
X is halogen;
at a pressure of less than about 10,000 psi with a phosphine of formula $P(R^9)_3$; wherein each $R^9$ is independently $C_{6-14}$ aryl; for a time and under conditions sufficient to prepare the compound of formula I. In some preferred embodiments processes for preparing a compound of formula I, the process further comprises a base, said base which is preferably non-nucleophilic, said non-nucleophilic base which is preferably isopropyldiethylamine.

In certain preferred embodiments of processes for preparing a compound of formula I, the process is carried out at a reaction pressure is in the range from about ambient to about 10,000 psi. In certain more preferred embodiments of processes for preparing a compound of formula I, the process is carried out at essentially ambient (atmospheric) pressure.

In certain preferred embodiments of processes for preparing a compound of formula I, the process is carried out at a reaction temperature is in the range of about 0° C. to about 200° C., preferably in the range of about 20° C. to about 140° C.

In other embodiments the invention is directed to compounds of the formula I:

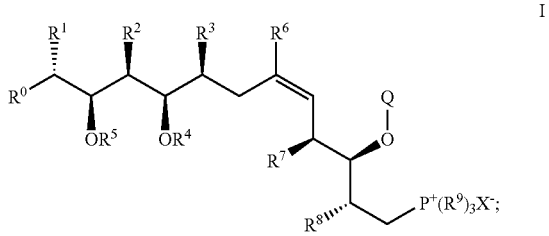

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;
$R^1$, $R^2$, $R^3$, $R^6$, $R^7$ and $R^8$ are independently H or $C_{1-10}$ alkyl;
$R^4$ is an acid labile hydroxyl protecting group;
$R^5$ is an oxidatively labile hydroxyl protecting group;
each $R^9$ is independently $C_{6-14}$ aryl;
Q is H or an acid labile hydroxyl protecting group wherein the hydroxyl protecting group has a mass of 135 Daltons or less and is unbranched at the atom bonded to the oxygen of the hydroxyl group being protected; and
X is halogen.

In yet other embodiments, the invention is directed to processes for preparing compounds of formula IIIa:

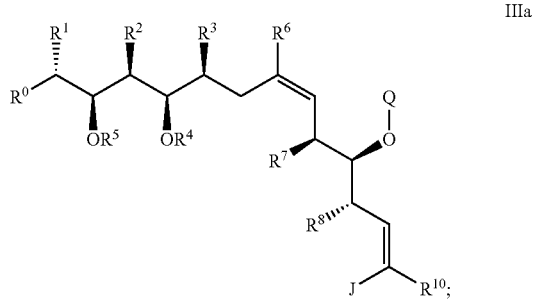

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;

$R^1$, $R^2$, $R^3$, $R^6$, $R^7$ and $R^8$ are independently H or $C_{1-10}$ alkyl;

$R^4$ is an acid labile hydroxyl protecting group;

$R^5$ is an oxidatively labile hydroxyl protecting group;

$R^{10}$ is H or $C_1$-$C_6$ alkyl;

Q is H or an acid labile hydroxyl protecting group wherein the hydroxyl protecting group has a mass of 135 Daltons or less and is unbranched at the atom bonded to the oxygen of the hydroxyl group being protected; and J is:

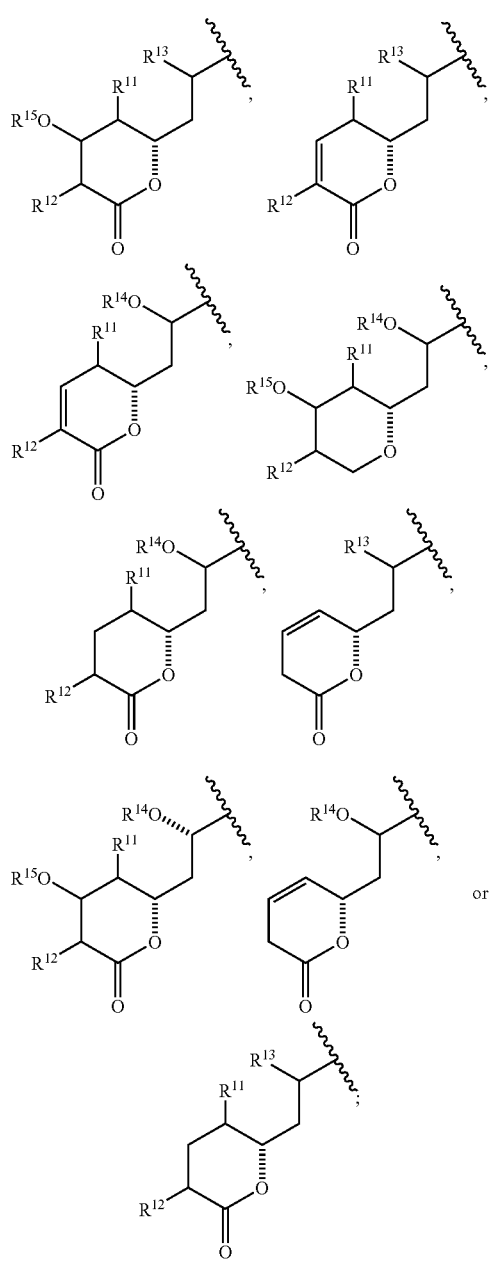

wherein:
$R^{11}$, $R^{12}$ and $R^{13}$ are each independently H or $C_1$-$C_{10}$ alkyl; and
$R^{14}$ and $R^{15}$ are each independently H or an acid labile hydroxyl protecting group;

comprising contacting a compound of formula I:

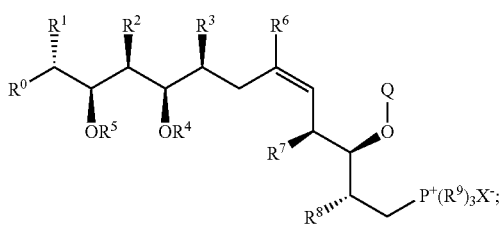

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;

$R^1$, $R^2$, $R^3$, $R^6$, $R^7$ and $R^8$ are independently H or $C_{1-10}$ alkyl;

$R^4$ is an acid labile hydroxyl protecting group;

$R^5$ is an oxidatively labile hydroxyl protecting group;

Q is H or an acid labile hydroxyl protecting group wherein the hydroxyl protecting group has a mass of 135 Daltons or less and is unbranched at the atom bonded to the oxygen of the hydroxyl group being protected;

each $R^9$ is independently $C_{6-14}$ aryl; and

X is halogen;

with a compound of formula J-C(=O)$R^{10}$;

wherein:
$R^{10}$ is H or $C_1$-$C_6$ alkyl; and
J is:

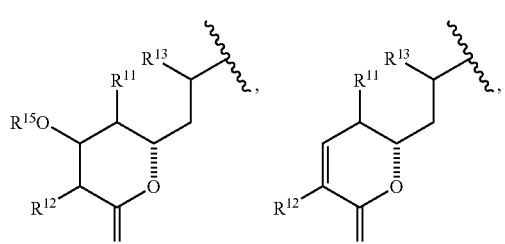

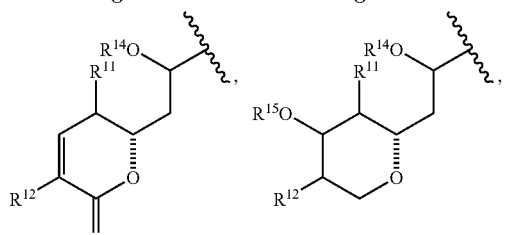

-continued

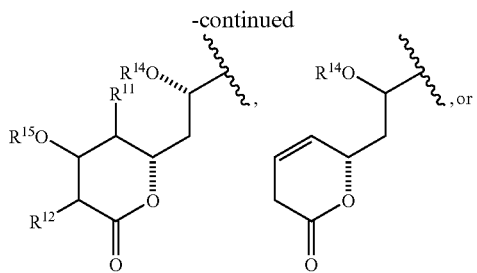

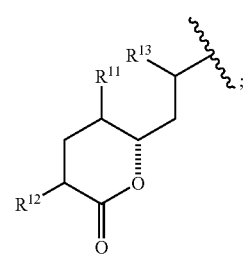

wherein:

$R^{11}$, $R^{12}$ and $R^{13}$ are each independently H or $C_1$-$C_{10}$ alkyl; and $R^{14}$ and $R^{15}$ are each independently H or an acid labile hydroxyl protecting group;

in the presence of a base for a time and under conditions sufficient to prepare the compound of formula IIIa.

In certain preferred embodiments of the invention directed to processes for preparing compounds of formula IIIa, at least one of $R^{14}$ and $R^{15}$ is other than H. In other preferred embodiments for preparing compounds of formula IIIa, the processes are carried out at a temperature in the range of about −30 to about −78° C.; more preferably at a temperature of about −78° C. In other preferred embodiments directed to preparing compounds of formula IIIa, the base is NaHMDS, LiHMDS, KHMDS, MeLi-LiBr complex, n-BuLi (with or without HMPA), KOtBu or NaH; more preferably, the base is $CH_3Li$—$CH_3Br$ complex.

In yet other preferred embodiments directed to, processes for preparing formula IIIa compounds the ratio of compounds of formula IIIa to compounds of formula IIIb is at least about 4; wherein the compounds of formula IIIa and IIIb have the structures:

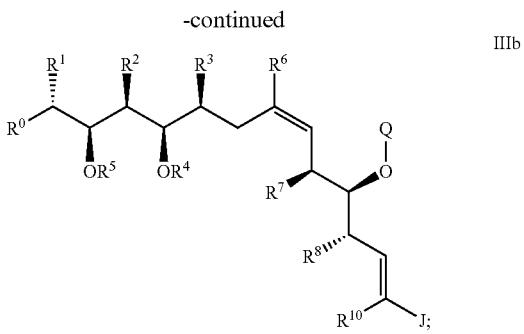

more preferably the ratio of formula IIIa compound to formula IIIb compounds is at least about 10.

In some preferred embodiments, $R^0$ is $C_{1-6}$ alkyl or $C_{2-6}$ alkenyl, more preferably $C_{2-6}$ alkenyl. In certain even more preferred embodiments, $R^0$ is:

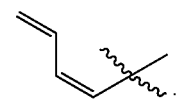

In some preferred embodiments, $R^1$, $R^2$, $R^1$, $R^6$, $R^7$ and $R^8$ are independently H or $C_{1-3}$ alkyl, more preferably H or $CH_3$. In other preferred embodiments $R^1$, $R^2$, $R^7$ and $R^8$ are $CH_3$ and $R^3$ and $R^6$ are each independently H or $C_{1-3}$ alkyl. Even more preferably when $R^1$, $R^2$, $R^7$ and $R^8$ are each $CH_3$, $R^3$ and $R^6$ are each independently H or $CH_3$. Yet more preferred, $R^1$, $R^2$, $R^3$, $R^7$ and $R^8$ are each $CH_3$ and $R^6$ is H or $CH_3$. Yet more preferred, $R^1$, $R^2$, $R^3$, $R^6$, $R^7$ and $R^8$ are each $CH_3$.

In some preferred embodiments, $R^4$ is $(R^{16})_3Si$-, wherein each $R^{16}$ is independently $C_{1-6}$ alkyl, more preferably $R^4$ is tert-butyldimethylsilyl (TBS) or triethylsilyl (TES). In alternative preferred embodiments, $R^4$ is Q.

In some preferred embodiments, $R^5$ ispara-methoxybenzyl (PMB).

In certain embodiments, at least one of $R^9$ is phenyl or substituted phenyl. In certain other embodiments each $R^9$ is independently phenyl or substituted phenyl. More preferably each $R^9$ is phenyl.

In some embodiments Q is H. In other embodiments, Q is an acid labile hydroxyl protecting group wherein the hydroxyl protecting group has a mass of 135 Daltons or less and is unbranched at the atom bonded to the oxygen of the hydroxyl group being protected. IN some preferred embodiments where Q is other than H, Q is methoxymethyl, methylthiomethyl, 2-methoxyethoxymethyl, acetyl, benzyloxymethyl, 2-(trimethylsilyl)ethoxymethyl or allyl; more preferably methoxymethyl.

In some embodiments, halogen is preferably iodo.

In some preferred embodiments, J is:

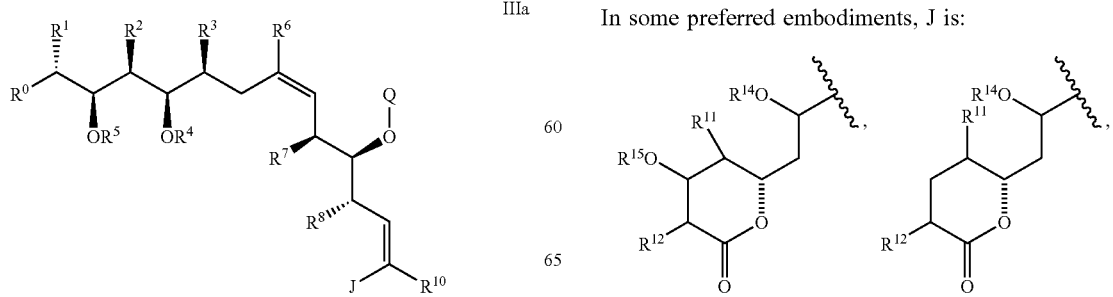

-continued

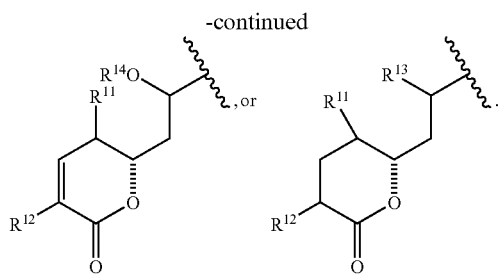

In some preferred embodiments $R^{10}$ is H or $C_{1-3}$ alkyl; preferably H or $CH_3$, even more preferably H.

In other preferred embodiments, $R^{11}$, $R^{12}$ and $R^{13}$ are each independently H or $C_1$-$C_3$ alkyl; more preferably H or $CH_3$. In yet other preferred embodiments, $R^{11}$ and $R^{12}$ are each independently H or $CH_3$ and $R^{13}$ is H. In some other embodiments $R^{11}$ and $R^{12}$ are each H. In yet other embodiments they are each $CH_3$.

In certain preferred embodiments, $R^{14}$ and $R^{15}$ are each independently an acid labile hydroxyl protecting group. In other preferred embodiments, at least one of $R^{14}$ and $R^{15}$ is H. In certain more preferred embodiments when $R^{14}$ or $R^{15}$ is an acid labile hydroxyl protecting group, the acid labile protecting group is tert-butyldimethylsilyl or triethylsilyl. In yet other preferred embodiments, at least one of $R^{14}$ and $R^{15}$ is Q; more preferably at least one of $R^{14}$ and $R^{15}$ is methoxymethyl.

The phosphonium salt derivatives of the present invention may be prepared according to the general method depicted in Scheme 2.

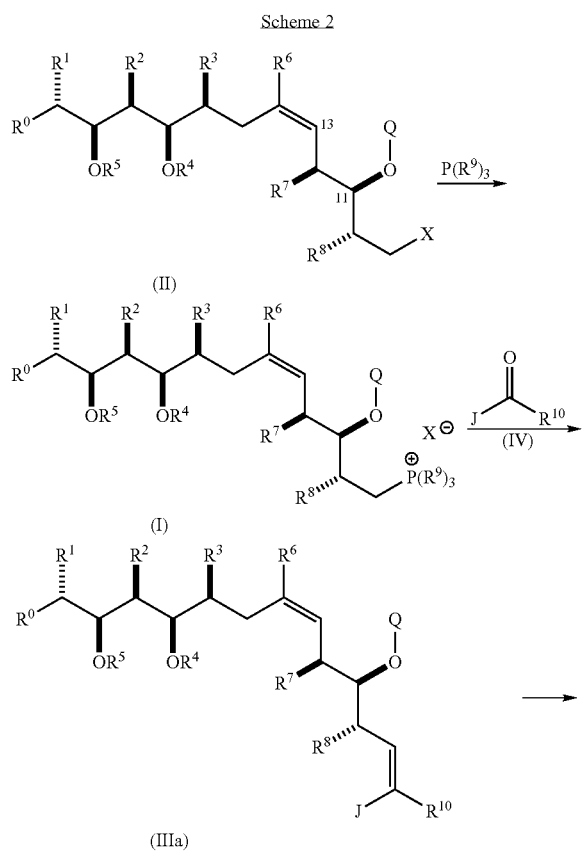

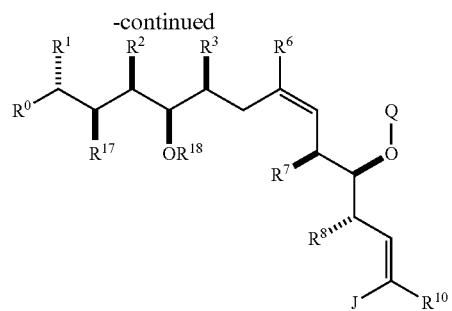

$R^{17}$ is -OH or $OC(=O)NR^{19}N^{20}$;
$R^{19}$ and $R^{20}$ are each independently H,
$C_{1-6}$ alkyl, $C_{2-6}$ alkenyl, $C_{2-6}$ alkynyl,
$(CH_2)_r$ ($C_{3-6}$ cycloalkyl), $(CH_2)_r$ (aryl) or
$(CH_2)_r$ (heterocycle),
wherein r is selected from 0, 1, 2, 3, and 4; and
$R^{18}$ is H or acid labile hydroxyl protecting group Treatment of alkyl halide II with triarylphosphine $P(R^9)_3$ under non-high pressure conditions in the presence of a base affords phosphonium salt II. Typical reaction times are between about 2 and about 24 hrs, reaction temperatures are between about room temperature ("RT") and about 140° C. A feature of the invention is that this reaction can be performed under non-high pressure conditions, by which is meant the reaction is conducted at pressures of about 10,000 psi or less, thus rendering unnecessary the use of unconventional high pressure equipment. Preferably, the base is Hünig's base (i-$PrNEt_2$), but other non-nucleophilic bases may also be used.

Reaction of phosphonium salt I with carbonyl compound IV in the presence of base yields compound IIIa having the discodermolide or a discodermolide analog scaffold. Typical reaction temperatures range from about −78° C. to about room temperature. Non-limiting examples of bases include NaHMDS, LiHMDS, KHMDS, MeLi-LiBr complex, n-BuLi (with or without HMPA), KOtBu, NaH and the like. Non-limiting examples of suitable solvents include THF, $ET_2O$, DME, DMF, and the like. The amount of carbonyl compound IV relative to phosphonium salt I ranges from about 0.25 to about 10, preferably from about 0.5 to about 2.0 equivalents, with about 1.0 equivalent being more preferred.

Compound IIIa can be further elaborated, for instance to make compound V, by one or more of the following actions: (a) removal of the various hydroxyl protecting groups; (b) removal of the oxidatively labile hydroxyl protecting group $R^5$; and (c) carbamoylation of the hydroxyl group resulting from the removal of $R^5$. Compound V corresponds to (+)-discodermolide itself when $R^0$ is butadienyl; $R^1$, $R^2$, $R^3$, $R^6$, $R^7$, and $R^8$ are each methyl; $R^{11}$ is H; $R^{10}$ is $OC(=O)NH_2$; and J is

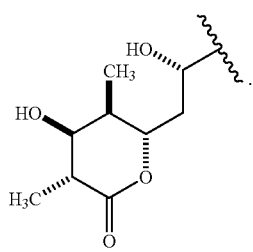

Examples of suitable J groups that are alkylaryl or alkylheteroaryl include:

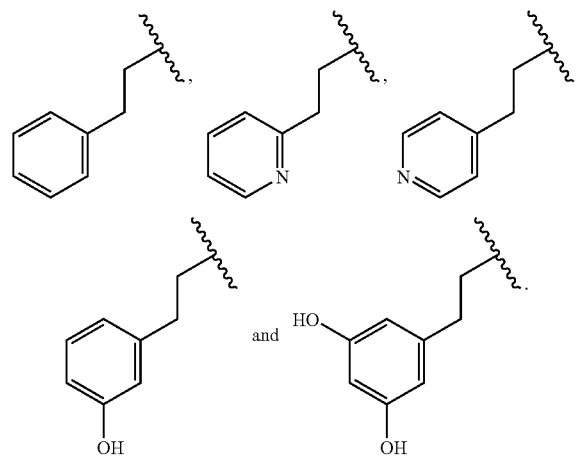

The feasibility of using a small protecting group Q or an unprotected hydroxyl at the C-11 precursor position to avoid or minimize cyclized by-products was demonstrated experimentally with model compound VII for the instances in which Q is acetyl, SEM, BOM, MOM, and H. Compounds VI were converted to intermediate iodo compound VII by treatment with triphenylphosphine (1.5 equivalents), imidazole (1.5 equivalents), and iodine (1.5 equivalents) in benzene-$Et_2O$ (1:2) at 0° C. to RT, for 3.5 hr. Iodo compound was in turn converted to Wittig salt VIII without isolation by adding more triphenylphosphine (10.0 equivalents) and i-$Pr_2$NEt (excess) at RT to approximately 100° C. for 17 hr.

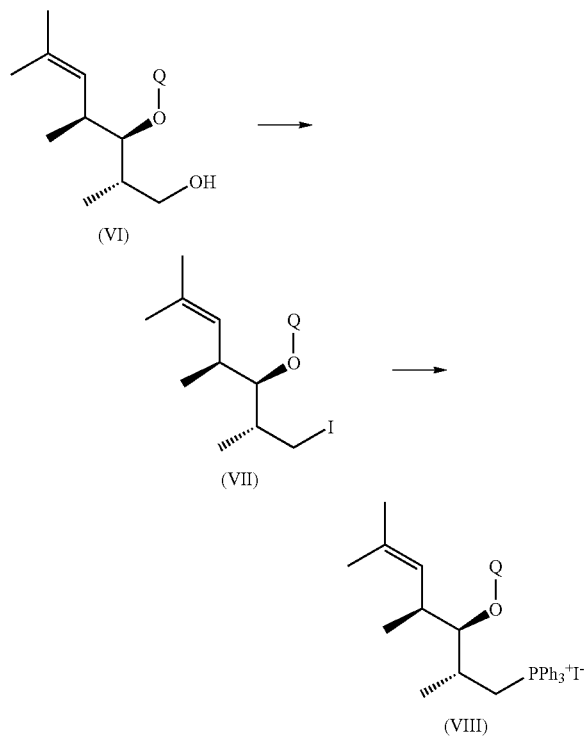

The results for the conversion of compounds VI to compounds VIII are summarized in Table I, following:

TABLE I

| Q | Yield (%, over 2 steps) |
|---|---|
| Acetyl | 59% |
| SEM | 63% |
| BOM | 70% |
| MOM | 69% |
| H | 62% |

Disclosures teaching techniques and compounds that can be used in the practice of this invention include Smith, III et al., U.S. Pat. No. 5,789,605 (1998); U.S. Pat. No. 6,031,133 (2000); U.S. Pat. No. 6,096,904 (2000); U.S. Pat. No. 6,242,616 B1 (2001); US 2002/0103387 A1; and WO 03/013502 A1; the disclosures of which are incorporated herein by reference.

The invention is further described by reference to the following specific examples. All of the examples are actual examples. These examples are for illustrative purposes only, and are not to be construed as limiting the appended claims. Those skilled in the art of organic synthesis may be aware of still other synthetic routes to the invention compounds. The reagents and intermediates used herein are either commercially available or prepared according to standard literature procedures. Example 12, 13, 15 and 16 are provided for comparative purposes only and do not illustrate processes of the present invention. Example 12 was carried out substantially in accordance with the procedures set forth in U.S. Pat. No. 6,242,616, which describes the preparation of trialkylsilyl-protected Wittig salts under extremely high pressure conditions. Example 13 was carried out substantially in accordance with the procedures set forth in U.S. Pat. No. 6,242,616 which describes the preparation of C-11 trialkylsilyl-protected Wittig salts except that the reaction was carried out under ambient pressure conditions. Example 15 was carried out substantially in accordance with the procedures set forth in U.S. Pat. No. 6,242,616 which specifically describes the preparation of C-11 Q-protected $\Delta^{8,9}$-double bond compounds. Example 16 was carried out substantially in accordance with the procedures set forth in U.S. Pat. No. 6,242,616 which describes the preparation of C-11 Bulky Silyl-protected $\Delta^{8,9}$-double bond compounds.

EXAMPLES

Reactions were carried out in oven or flame-dried glassware under an argon atmosphere, unless otherwise noted. All solvents were reagent grade. Diethyl ether ($Et_2O$) and tetrahydrofuran (THF) were freshly distilled from sodium/benzophenone under argon. n-Butyllithium and t-butyllithium were purchased from Aldrich. Reactions were magnetically stirred and monitored by thin layer chromatography (TLC) with 0.25 mm E. Merck pre-coated silica gel plates. Flash chromatography was performed with silica gel 60 (particle size 0.040-0.062 mm) supplied by Silicycle and Sorbent Technologies. Yields refer to chromatographically and spectroscopically pure compounds, unless otherwise stated. Infrared spectra were recorded on a Jasco Model FT/IR-480 Plus spectrometer. Proton and carbon-13 NMR spectra were recorded on a Bruker AMX-500 spectrometer. Chemical shifts are reported relative to either chloroform ($\delta$ 7.26) or benzene ($\delta$ 7.15) for $^1$H-NMR and either chloroform ($\delta$ 77.0) or benzene ($\delta$ 128.0) for $^{13}$C NMR. Optical rotations were measured on a Perkin-Elmer model 241 polarimeter. High resolution mass spectra were measured at the University of Pennsylvania Mass Spectrometry Service Center. Preparation of aldehyde (−)-C used in Examples 14, 15, and 16 can be found in Smith, et al., U.S. Pat. No. 6,096,904. Preparation of the common precursor (−)-CP used in the Example 1 can be found in Smith, et al., U.S. Pat. No. 6,031,133.

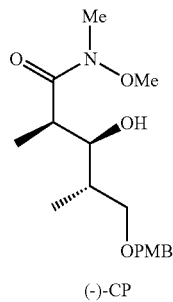

(−)-CP (+)-Discodermolide System (Beginning from (−)-CP)

Example 1

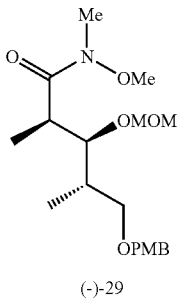

(−)-29

MOM Ether (−)-29. A solution of common precursor (−)-CP (7.0 g, 21.6 mmol) and i-Pr$_2$NEt (7.5 mL, 43.2 mmol) in CH$_2$Cl$_2$ (210 mL) was cooled to 0° C. and MOMCl (2.42 mL, 32.0 mmol) was added. The common precursor is the structure bearing a free hydroxyl in place of the OMOM group in 29. The mixture was stirred for 2 h, at which time another portion of MOMCl was added (this was repeated until no starting material remained). The reaction was quenched by addition of a saturated aqueous solution of NH$_4$Cl (50 mL). The aqueous layer was extracted (3×100 mL of Et$_2$O), and the combined organic layers were washed with water, saturated NaHCO$_3$ (2×50 mL), and brine. The organic layer was dried over MgSO$_4$, filtered, and concentrated to yield (−)-29 (7.5 g, 95%) as a clear, colorless oil. The product was purified via flash chromatography (15% ethyl acetate/hexanes): $[\alpha]_D^{23}$ −20.8° (c 4.8, CHCl$_3$); IR (NaCl) 2937, 1662, 1612, 1513, 1464, 1379, 1248, 1090, 1034 cm$^{-1}$; $^1$H-NMR (500 MHz, CDCl$_3$) δ 7.23 (d, J=8.7 Hz, 2H), 6.84 (d, J=8.6 Hz, 2H), 4.61 (ABq, J$_{AB}$=6.54 Hz, Δν$_{AB}$=17.3 Hz, 2H), 4.39 (s, 2H), 3.78 (s, 3H), 3.76 (dd, J=6.1, 4.8 Hz, 1H), 3.58 (s, 3H), 3.56 (d, J=4.8 Hz, 1H), 3.34 (s, 3H), 3.27 (dd, J=9.1, 7.1 Hz, 1H), 3.13 (m, 1H), 3.12 (s, 3H), 1.97-1.91 (m, 1H), 1.15 (d, J=6.9 Hz, 3H), 1.03 (d, J=6.9 Hz, 3H); $^{13}$C-NMR (125 MHz, CDCl$_3$) δ 176.8, 159.0, 130.7, 129.1, 113.4, 98.3, 82.3, 72.7, 71.8, 61.0, 56.1, 55.1, 38.4, 37.1, 32.2, 15.2, 12.9; high resolution mass spectrum (ES$^+$) m/z 392.20554 [(M+Na)$^+$; calcd for C$_{19}$H$_{31}$NO$_6$: 392.204908].

Example 2

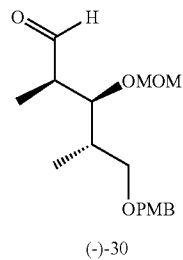

(−)-30

Aldehyde (−)-30. At −10° C., a solution of amide (−)-29 (3.9 g, 10.5 mmol) in THF (105 mL) was treated with DIBAL-H (1.0 M in toluene, 12.7 mL) via drop-wise addition down the side of the flask (10 min. addition time). The reaction was stirred for an additional 3 h and quenched with MeOH (1 mL). The −10° C. reaction mixture was poured into saturated aqueous Rochelle's salt (100 mL), diluted with Et$_2$O (150 mL), and stirred at room temperature for 30 min. The mixture was then poured into a separatory funnel and vigorously shaken (emulsion). The layers were separated, and the organic layer was washed with saturated aqueous Rochelle's salt, water, saturated NaHCO$_3$, and brine (1×100 mL each). The organic layer was dried over MgSO$_4$, filtered, and concentrated to give (−)-30 (3.2 g, 99%) as a clear, colorless oil, which was taken onto the next step without further purification. An analytical sample was obtained via flash chromatography (15% EtOAc/hexanes): $[\alpha]_D^{23}$ −30.1° (c 6.5, CHCl$_3$); IR (CHCl$_3$) 2938, 2901, 1513, 1248, 1726 cm$^{-1}$; $^1$H-NMR (500 MHz, CDCl$_3$) δ 9.70 (s, 1H), 7.24 (d, J=8.6 Hz, 2H), 6.87 (d, J=8.6 Hz, 2H), 4.60 (d, J=6.8 Hz, 1H), 4.49 (d, J=6.8 Hz, 1H), 4.41 (s, 2H), 4.06 (dd, J=8.5, 3.0 Hz, 1H), 3.80 (s, 3H), 3.49 (dd, J=8.9, 5.0 Hz, 1H), 3.44 (dd, J=8.9, 4.1 Hz, 1H), 3.23 (s, 3H), 2.50 (ddd, J=14.0, 6.8, 2.6 Hz, 1H), 2.03-1.95 (m, 1H), 1.11 (d, J=7.0 Hz, 3H), 1.00 (d, J=7.0 Hz, 3H); $^{13}$C-NMR (125 MHz, CDCl$_3$) δ 203.9, 159.1, 130.4, 129.1, 113.7, 97.7, 78.9, 72.7, 71.4, 55.6, 55.2, 48.6, 36.6, 14.5, 6.9; high resolution mass spectrum (FAB, NBA) m/z 333.1665 [(M+Na)$^+$; calcd for C$_{17}$H$_{26}$O$_5$Na: 333.16775].

Example 3

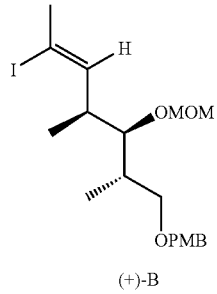

(+)-B (+)-Fragment B. At 0° C., a suspension of EtPh3PI (1.34 g, 3.06 mmol, dried at 70° C./0.2 Torr for 2 h) in THF (11 mL, dried over 4 Å MS, sparged with argon) was treated with n-BuLi (2.4 M in hexanes, 1.27 mL, 3.06 mmol) over 30 min. to form a dark red solution. After an additional 10 min., the red ylide was added over 10 min. via cannula to a cooled (−78° C.) solution of $I_2$ (774 mg, 3.06 mmol) in THF (27 mL solution, prepared by adding $I_2$ to degassed THF at rt and vigorously stirring for 40 min. before cooling) such that the internal temperature did not exceed −70° C. The resultant yellow slurry was stirred at −75° C. (internal) for 5 min. and warmed to −23° C. (internal). NaHMDS (1.0 M in THF, 2.75 mL) was added via cannula over 30 min., and the resulting orange suspension was stirred 15 min. further and cooled to −33° C. (internal). A solution of the crude aldehyde (−)-30 (475 mg, 1.53 mmol) in THF (5 mL) was introduced via cannula over 15 min., and the reaction mixture was stirred at −30° C. for an additional 45 min., warmed to 7° C. over 1 h, and quenched with MeOH (2 mL). The mixture was then suction filtered through a 6 to 8" silica plug (100% $Et_2O$, 20 mL sintered glass frit), the filtrate was washed with saturated aqueous $Na_2S_2O_3$ and brine, dried over $MgSO_4$, filtered, and concentrated. Flash chromatography (15% $CH_2Cl_2$/hexanes; then gradient elution 2% ethyl acetate/hexanes→5% ethyl acetate/hexanes) furnished (+)-B (190 mg, 40% yield for two steps, 9:1 Z/E) as a clear, colorless oil. An analytical sample of the Z isomer was obtained by flash chromatography (2% ethyl acetate/hexanes): $[60]_D^{23}$ +9.20 (c 2.5, $CHCl_3$); IR 2965, 2929, 2849, 1612, 1512, 1456, 1247, 1090, 1034 $cm^{-1}$; $^1$H-NMR (500 MHz, $CDCl_3$) δ 7.25 (d, J=8.6 Hz, 2H), 6.87 (d, J=8.6 Hz, 2H), 5.35 (dd, J=8.9, 1.5 Hz, 1H), 4.61 (d, J=6.6 Hz, 1H), 4.58 (d, J=6.6 Hz, 1H), 4.42 (s, 2H), 3.80 (s, 3H), 3.52 (dd, J=9.1, 4.3 Hz, 1H), 3.38 (apparent t, J=5.7 Hz, 1H), 3.37 (s, 3H), 3.35 (dd, J=9.1, 2.0 Hz, 1H), 2.60-2.56 (m, 1H), 2.46 (d, J=1.5 Hz, 3H), 1.99 (ddd, J=10.4, 6.8, 4.3 Hz, 1H), 1.04 (d, J=6.9 Hz, 3H), 0.99 (d, J=6.8 Hz, 3H); $^{13}$C-NMR (125 MHz, $CDCl_3$) δ 159.0, 138.5, 130.7, 129.1, 113.6, 99.5, 98.1, 83.7, 72.6, 72.0, 55.9, 55.2, 43.6, 36.7, 33.5, 14.8, 14.2; high resolution mass spectrum (FAB, NBA) m/z 471.099989 [(M+Na)$^+$; calcd for $C_{19}H_{29}IO_4Na$: 471.100831].

Example 4

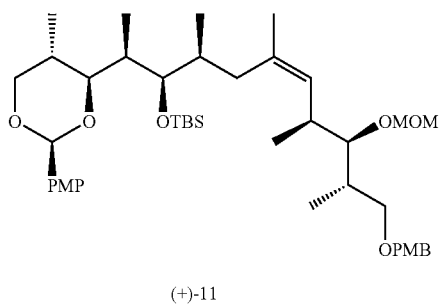

(+)-11

(+)-11 (Modified Negishi Coupling). A 1.0 M solution of anhydrous $ZnCl_2$ (11.91 mL, 1.92 mmol) was added via syringe to a solution of alkyl iodide (+)-A (1.05 g, 1.9 mmol) in dry $Et_2O$ (8 mL), and the resulting solution was cooled to −78° C. and degassed by briefly pumping and backfilling with argon. t-BuLi (1.7 M in pentane, 13.8 mL, 5.7 mmol) was added via syringe over 12 min. The resulting solution was stirred 5 min. further, evacuated (1×0.1 torr) and again back-filled with argon. The −78° C. bath was then removed, and the reaction was stirred at ambient temperature for 1 h. The resulting cloudy suspension was transferred by cannula into an intimate mixture of vinyl iodide (+)-B (0.750 g, 1.67 mmol; 9:1 Z/E) and $Pd(PPh_3)_4$ (0.140 g, 0.13 mmol). The reaction mixture was stirred overnight in the absence of light, and quenched via slow addition of the reaction mixture to water (20 mL). The mixture was diluted with $Et_2O$, and the layers were separated. The aqueous layer was extracted (3×$Et_2O$), and the combined organic layers were washed (saturated aqueous $NaHCO_3$, brine), dried ($MgSO_4$), filtered and concentrated. Flash chromatography (gradient elution: 2% EtOAc/hexanes→5% EtOAc/hexanes) provided (+)-11 as a light orange oil (0.997 g, 80% yield, 90% based on purity of vinyl iodide): $[α]_D^{23}$ +30.0° (c 0.5, $CHCl_3$); IR (NaCl) 2958, 2931, 2872, 2854, 1615, 1516, 1461, 1388, 1249, 1035 $cm^{-1}$; $^1$H-NMR (500 MHz, $CDCl_3$) δ 7.37 (d, J=8.7 Hz, 2H), 7.24 (d, J=8.6 Hz, 2H), 6.86 (apparent t, J=8.2 Hz, 4H), 5.39 (s, 1H), 5.05 (d, J=9.7 Hz, 1H), 4.61 (ABq, $J_{AB}$=6.3 Hz, $Δν_{AB}$=14.9 Hz, 2H), 4.39 (ABq, $J_{AB}$=11.5 Hz, $Δν_{AB}$=17.1 Hz, 2H), 4.09 (dd, J=11.2, 4.5 Hz, 1H), 3.80 (s, 3H), 3.79 (s, 3H), 3.63 (dd, J=7.1, 1.9 Hz, 1H), 3.51 (m, 2H), 3.48 (apparent t, J=8.9 Hz, 1H), 3.37 (s, 3H), 3.30 (dd, J=8.9, 7.8 Hz, 1H), 3.22 (apparent t, J=5.9 Hz, 1H), 2.61 (ddd, J=10.1, 6.7, 6.7 Hz, 1H), 2.31 (apparent t, J=12.3 Hz, 1H), 2.1-1.9 (m, 3H), 1.89 (ddd, J=7.1, 7.1, 1.8 Hz, 1H), 1.71 (br d, J=12.3 Hz, 1H), 1.57 (s, 3H), 1.01 (d, J=7.1 Hz, 3H), 0.99 (d, J=7.1 Hz, 3H), 0.94 (d, J=6.7 Hz, 3H), 0.91 (s, 9H), 0.75 (d, J=7.1 Hz, 3H), 0.74 (s, 3H), 0.09 (s, 3H), 0.42 (s, 3H); $^{13}$C-NMR (125 MHz, $CDCl_3$) δ 159.7, 159.0, 132.8, 131.5, 130.9, 130.3, 129.0, 127.2, 113.7, 113.4, 101.0, 98.2, 85.3, 83.3, 78.4, 73.2, 72.5, 72.3, 56.0, 55.2, 38.1, 37.6, 36.7, 34.5, 33.7, 30.7, 26.1, 26.2, 18.4, 16.3, 14.8, 12.6, 12.1, 10.8, −3.5, −3.9; high resolution mass spectrum (ES+) m/z 765.4767 [(M+Na)$^+$; calcd for $C_{43}H_{70}O_8SiNa$: 765.4738].

Example 5

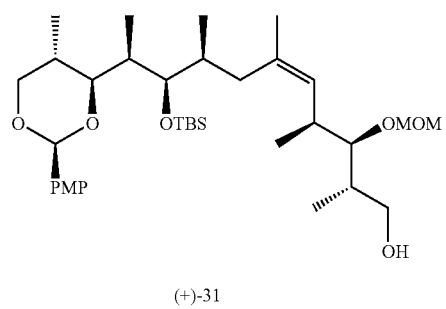

(+)-31

Alcohol (+)-31 (Chemoselective Hydrolysis of PMB Ether). At 0° C., a solution of PMB ether (+)-11 (850 mg, 1.14 mmol) in $CH_2Cl_2$ (10.5 mL) was treated with $H_2O$ (0.5 mL), DDQ (312 mg, 1.37 mmol) and stirred for 3 h. The mixture was quenched with 2 mL of saturated $NaHCO_3$, washed with $H_2O$ (2×10 mL) and the layers were separated. The aqueous layer was then extracted with $CH_2Cl_2$ (2×10 mL). The combined organic extracts were dried ($MgSO_4$), filtered, concentrated and chromatographed (10% EtOAc/hexanes) to provided 630 mg (+)-31 (93%); mp: 65-68° C.; $[α]_D^{23}$ +18.6° (c 6.8, $CHCl_3$); IR ($CHCl_3$) 3509, 2923, 1739, 1615, 1518, 1461, 1388, 1302, 1253 $cm^{-1}$; $^1$H-NMR (500 MHz, $CDCl_3$) δ 7.37 (d, J=8.7 Hz, 2H), 6.86 (d, J=8.7 Hz, 2H), 5.38 (s, 1H), 5.05 (d, J=10.0 Hz, 1H), 4.66 (d, J=6.5 Hz, 1H), 4.64 (d, J=6.5 Hz, 1H), 4.09 (dd, J=11.2, 4.7 Hz, 1H), 3.84-3.80 (m, 1H), 3.80 (s, 3H), 3.63 (dd, J=7.1, 1.8 Hz, 1H), 3.51 (dd, J=9.9, 1.7 Hz, 1H), 3.50-3.46 (m, 2H), 3.42 (s, 3H), 3.26 (dd, J=7.0, 5.1 Hz, 1H), 2.69 (dd, J=7.6, 5.2 Hz, 1H), 2.64 (dd, J=6.3, 1.6 Hz, 1H), 2.30 (apparent t, J=12.2 Hz, 1H), 2.09-2.03 (m, 1H), 2.03-1.95 (m, 1H), 1.89 (ddd, J=7.0, 7.0, 1.7 Hz, 1H), 1.79 (dddd, J=17.6, 7.1, 7.1, 3.3 Hz, 1H), 1.74 (br d, J=12.7 Hz, 1H), 1.60 (s, 3H), 1.02 (d, J=7.2 Hz, 3H), 1.01 (d, J=7.0 Hz, 3H), 0.94 (d, J=6.7 Hz, 3H), 0.91 (s, 9H), 0.76 (d, J=6.9 Hz, 3H), 0.74 (d, J=6.7 Hz, 3H), 0.05 (s, 3H), 0.01 (s, 3H); $^{13}$C-NMR (125 MHz, CDCl$_3$) δ 159.7, 133.3, 131.4, 130.0, 127.2, 113.3, 100.9, 99.0, 87.2, 83.3, 73.2, 65.0, 56.2, 55.1, 38.1, 37.6, 37.3, 34.6, 33.8, 30.7, 26.1, 23.2, 18.3, 15.2, 15.0, 12.5, 12.0, 10.7, −3.5, −3.8; high resolution mass spectrum (CI, NH$_3$) m/z 645.417132 [(M+Na)$^+$; calcd for C$_{35}$H$_{62}$O$_7$SiNa: 645.416253.

Example 6

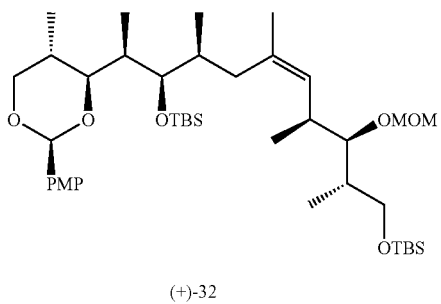

(+)-32

Silyl protected anisylidene acetal (+)-32. To a solution of alcohol (+)-31 (624 mg, 1.00 mmol) in CH$_2$Cl$_2$ (10 mL) was added imidazole (137.8 mg, 2.02 mmol) and TBS-Cl (227.9 mg, 1.52 mmol). The mixture was stirred for 1 h at ambient temperature. The reaction was then quenched with a brine solution, extracted with CH$_2$Cl$_2$ (3×10 mL), and washed with H$_2$O (10 mL). The organic layers were separated, dried (MgSO$_4$), filtered, and concentrated in vacuo. Flash chromatography (10% EtOAc/hexanes) provided (+)-32 (723 mg, 98%); [α]$_D^{23}$ +28.2° (c 3.5, CHCl$_3$) IR (CHCl$_3$) 2964, 2931, 2861, 1618, 1520, 1466, 1390, 1248 cm$^{-1}$; $^1$H-NMR (500 MHz, CDCl$_3$) δ 7.37 (d, J=8.6 Hz, 2H), 6.87 (d, J=8.6 Hz, 2H), 5.38 (s, 1H), 5.10 (d, J=9.9 Hz, 1H), 4.64 (d, J=6.4 Hz, 1H), 4.61 (d, J=6.5 Hz, 1H), 4.10 (dd, J=11.2, 4.7 Hz, 1H), 3.80 (s, 3H), 3.65-3.63 (m, 2H), 3.54-3.44 (m, 3H), 3.40 (s, 3H), 3.21 (apparent t, J=5.9 Hz, 1H), 2.58 (ddd, J=16.2, 12.2, 6.0 Hz, 1H), 2.32 (apparent t, J=12.2 Hz, 1H) 2.10-2.04 (m, 1H), 2.04-1.94 (m, 1H), 1.92-1.85 (m, 1H), 1.83 (br ddd J=13.9, 6.9,4.2 Hz, 1H), 1.75 (apparent d, J=12.0 Hz, 1H), 1.60 (s, 3H), 1.01 (d, J=7.0 Hz, 3H), 0.94 (d, J=6.6 Hz, 3H), 0.94 (d, J=6.9 Hz, 3H), 0.90 (s, 9H), 0.88 (s, 9H), 0.76 (d, J=6.9 Hz, 3H), 0.74 (d, J=6.7 Hz, 3H), 0.04 (s, 3H), 0.02 (app s, 6H), 0.01 (s, 3H); $^{13}$C-NMR (125 MHz, CHCl$_3$) δ 159.7, 132.5, 131.4, 130.5, 127.8, 113.3, 101.0, 98.1, 84.7, 83.4, 78.3, 73.2, 64.8, 56.0, 55.1, 38.9, 38.0, 37.4, 34.1, 33.7, 30.7, 26.1, 25.8, 23.1, 18.3, 18.2, 14.1, 12.6, 12.0, 10.7, −3.4, −3.9; high resolution mass spectrum (ES$^+$) m/z 759.506365 [(M+Na)$^+$; calcd for C$_4$OH$_{76}$O$_7$SiNa: 759.502732].

Example 7

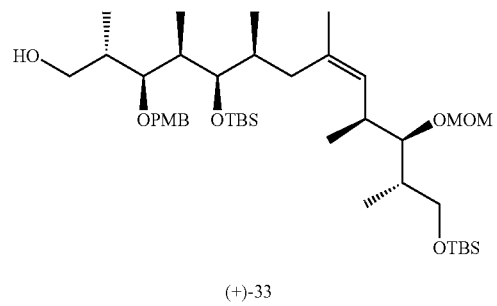

(+)-33

Silyl protected alcohol (+)-33. To a −50° C. solution of silyl ether (+)-32 (724 mg, 0.98 mmol) in CH$_2$Cl$_2$ (10 mL) was added DIBAL-H (1 M in toluene, 3.9 mL, 3.9 mmol). The resulting solution was stirred for 24 h, quenched via dropwise addition of pH 7.0 buffer (20 mL), and then diluted with CH$_2$Cl$_2$ (20 mL). The mixture was then added to 50 mL of saturated sodium potassium tartrate solution, extracted with CH$_2$Cl$_2$ (4×30 mL), and the layers separated. The organic layer was washed with H$_2$O (50 mL), dried (MgSO$_4$), filtered, and concentrated. Flash chromatography (20% EtOAc/hexanes) provided 615 mg (+)-33 (85%) as a white foam: [α]$_D^{23}$ +3.8 (c 2.6, CHCl$_3$); IR (CHCl$_3$) 3474, 2957, 2929, 2856, 1612, 1514, 1472, 1387, 1250, 1089, 1036 cm$^{-1}$; $^1$H-NMR (500 MHz, CDCl$_3$) δ 7.26 (d, J=8.7 Hz, 2H), 6.87 (d, J=8.7 Hz, 2H), 5.12 (d, J=10.0 Hz, 1H), 4.65 (d, J=6.4 Hz, 1H), 4.61 (d, J=6.5 Hz, 1H), 4.53 (d, J=10.5 Hz, 1H), 4.49 (d, J=10.4 Hz, 1H), 3.80 (s, 3H), 3.75 (ddd, J=11.0, 5.2, 3.5 Hz, 1H), 3.63 (dd, J=9.7, 4.2 Hz, 1H), 3.58 (dt, J=11.0, 5.5 Hz, 1H), 3.54 (dd, J=5.1, 3.6 Hz, 1H), 3.48 (dd, J=9.8, 7.4 Hz, 1H), 3.40 (s, 3H), 3.35 (apparent t, J=5.5 Hz, 1H), 3.21 (apparent t, J=5.8 Hz, 1H), 2.73 (apparent t, J=5.6 Hz, 1H), 2.57 (dq, J=12.8, 6.4 Hz, 1H), 2.24 (apparent t, J=12.3 Hz, 1H), 2.00-1.88 (m, 3H), 1.86-1.80 (m, 2H), 1.64 (s, 3H), 1.05 (d, J=7.2 Hz, 3H), 1.03 (d, J=7.1 Hz, 3H), 0.96-0.92(m, 6H) 0.94 (s, 9H), 0.88 (s, 9H), 0.75 (d, J=6.7 Hz, 3H), 0.08 (s, 6H), 0.02 (br s, 6H); $^{13}$C-NMR (125 MHz, CDCl$_3$) δ 159.2, 132.1, 130.9, 130.2, 129.3, 113.8, 98.1, 86.3, 84.7, 77.3, 75.2, 65.2, 64.8, 56.0, 55.2, 39.7, 38.4, 37.3, 36.5, 35.2, 34.2, 26.1, 25.8, 23.1,1 8.4, 18.2, 16.0, 15.6, 14.1, 13.6, 11.4, −3.2, −3.5, −5.4 (2); high resolution mass spectrum (ES$^+$) m/z 761.516364 [(M+Na)$^+$; calcd for C$_{41}$H$_{78}$O$_7$Si$_2$Na: 761.518382].

Example 8

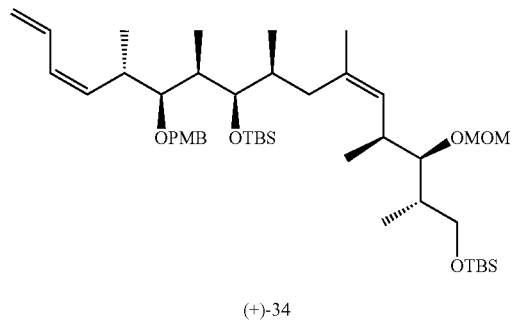

(+)-34

Silyl Protected Triene 34. To a 0° C. solution of alcohol (+)-33 (160 mg, 0.21 mmol) in CH$_2$Cl$_2$ (2.1 mL) was added Dess-Martin periodinane (87.4 mg, 0.23 mmol) and NaHCO$_3$ (47.4 mg, 0.63 mmol). The resulting solution was stirred for 2.5 h and quenched with saturated NaS$_2$O$_3$ solution (2 mL) and saturated NaHCO$_3$ solution (2 mL). The mixture was then extracted with Et$_2$O (3×10 mL) and the layers were separated. The organic layer was then washed with H$_2$O, dried (MgSO$_4$), filtered, and concentrated. The resulting white foam 12 was used without further purification. An analytical sample was obtained via flash chromatography (3% EtOAc/hexanes): Aldehyde 12: IR (CHCl$_3$) 2953, 2926, 2861, 1716, 1515, 1460, 1253 cm$^{-1}$; $^1$H-NMR (500 MHz, CDCl$_3$) δ 9.80 (d, J=2.5 Hz, 1H), 7.22 (d, J=8.6 Hz, 2H), 6.80 (d, J=8.6 Hz, 2H), 5.13 (d, J=9.8 Hz, 1H), 4.65 (d, J=6.5 Hz, 1H), 4.61 (d, J=6.5 Hz, 1H), 4.47 (s, 2H), 3.79 (s, 3H), 3.64 (dd, J=9.9, 4.3 Hz, 1H), 3.60 (dd, J=5.3, 3.2 Hz, 1H), 3.57 (apparent t, J=5.4 Hz, 1H), 3.49 (dd, J=9.3, 7.1 Hz, 1H), 3.41 (s, 3H), 3.22 (apparent t, J=5.8 Hz, 1H), 2.74 (ddd, J=15.2, 7.0, 2.6 Hz, 1H), 2.57 (ddd, J=16.8, 13.1, 6.5 Hz, 1H), 2.25 (apparent t, J=12.5 Hz, 1H), 2.00-1.88 (m, 2H), 1.98-1.81 (m, 1H), 1.78 (bd, J=13.1 Hz, 1H), 1.63 (s, 3H), 1.12 (d, J=7.0 Hz, 3H), 1.04 (d, J=6.9 Hz, 3H), 0.96-0.93 (m, 6H), 0.93 (s, 9H), 0.89 (s, 9H), 0.76 (d, J=6.7 Hz, 3H), 0.08 (s, 3H), 0.07 (s, 3H), 0.03 (s, 6H); $^{13}$C-NMR (125 MHz, CDCl$_3$) δ 204.4, 159.2, 131.9, 131.0, 130.2, 129.0, 113.7, 98.1, 84.7, 82.6, 77.0, 76.6, 74.3, 64.8, 56.0, 55.1, 49.4, 40.1, 38.8, 36.5, 35.0, 34.2, 26.1, 25.8, 23.1, 18.4, 18.2, 16.0, 14.1, 13.4, 12.1, 11.3, −3.2, −3.6, −5.4; high resolution mass spectrum (ES$^+$) m/z 759.506140 [(M+Na)$^+$; calcd for C$_{41}$H$_{76}$O$_7$Si$_2$Na: 759.502732].

To a −78° C. solution of freshly distilled allyldiphenylphosphine (95 μL, 0.44 mmol) in THF (2.1 mL, degassed) was added 270 μL of t-butyllithium (1.7 M in pentane, 0.44 mmol) and the solution was stirred for 5 min. The solution was warmed to 0° C., stirred for 30 min. and cooled to −78° C. The solution was then treated with freshly distilled Ti(Oi-Pr)$_4$ (131 μL, 0.44 mmol) and stirred for 30 min. A precooled (−78° C.) solution of aldehyde 12 (160 mg, 0.217 mmol) in THF (2 mL) was added via cannula (rinse 1×2 mL), stirred for 1 h, and then warmed to 0° C. Iodomethane (0.13 mL, 2.17 mmol) was added, and the solution was warmed to ambient temperature and stirred for 16 h. The solution was quenched with pH 7.0 buffer (2 mL) and extracted with CH$_2$Cl$_2$ (3×10 mL) and Et$_2$O (3×10 mL). The combined organic layers were washed with brine, dried (MgSO$_4$), filtered, and concentrated. Flash chromatography (2% EtOAc/hexanes) provided (+)-34 (102 mg, 66% from (+)-33, 14:1 mixture of Z:E isomers) as a white foam: [α]$_D^{23}$ +30.0 (c 1.0, CHCl$_3$); IR (CHCl$_3$) 3060, 2940, 1600, 1450 cm$^{-1}$; $^1$H-NMR (500 MHz, CDCl$_3$, Z isomer) δ 7.28 (d, J=8.6 Hz, 2H), 6.87 (d, J=8.6 Hz, 2H), 6.56 (ddd, J=16.8, 10.6, 10.6 Hz, 1H), 6.02 (apparent t, J=11.0 Hz, 1H), 5.58 (apparent t, J=10.5 Hz, 1H), 5.20 (dd, J=16.8, 1.3 Hz, 1H), 5.10 (m, 2H), 4.65 (d, J=6.5 Hz, 1H), 4.62 (d, J=6.5 Hz, 1H), 4.57 (d, J=10.6 Hz, 1H), 4.47 (d, J=10.6 Hz, 1H), 3.80 (s, 3H), 3.64 (dd, J=9.6, 4.3 Hz, 1H), 3.52-3.46 (m, 2H), 3.41 (s, 3H), 3.25 (dd, J=7.1, 3.9 Hz, 1H), 3.21 (apparent t, J=5.8 Hz, 1H), 3.04-2.96 (m, 1H), 2.58-2.52 (m, 1H), 2.09 (apparent t, J=12.2 Hz, 1H), 1.88-1.79 (m, 3H), 1.75 (br d, J=13.0 Hz, 1H), 1.60 (s, 3H), 1.10 (d, J=6.8 Hz, 3H), 1.02 (d, J=6.8 Hz, 3H), 0.96 (s, 9H), 0.94 (d, J=6.8 Hz, 3H), 0.93 (d, J=6.5 Hz, 3H), 0.90 (s, 9H), 0.74 (d, J=6.7 Hz, 3H), 0.11 (s, 3H), 0.10 (s, 3H), 0.04 (s, 3H), 0.04 (s, 3H); $^{13}$C-NMR (125 MHz, CDCl$_3$, Z isomer) δ 159.0, 134.5, 132.3, 132.3, 131.1, 130.6, 129.0, 128.9, 117.0, 113.6, 98.0, 84.7, 84.5, 77.0, 74.8, 64.9, 55.9, 55.1, 40.0, 38.9, 36.1, 35.4, 35.3, 34.1, 26.2, 25.9, 23.0, 18.6, 18.2, 18.1, 16.0, 14.3, 14.0, 10.7, −3.2, −3.4, −5.4 (2); high resolution mass spectrum (ES$^+$) m/z 783.5400 [(M+Na)$^+$; calcd for C$_{44}$H$_{80}$O$_6$Si$_2$Na: 783.5391].

Example 9

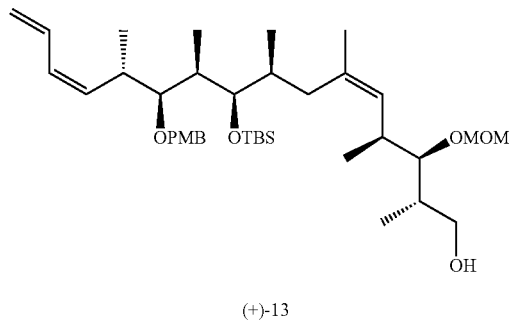

(+)-13

MOM ether (+)-13. Bis-TBS alcohol (+)-34 (211.1 mg, 0.278 mmol) was dissolved in a 1.0% conc. HCl/EtOH solution (9.3 mL) (37% HCl solution:EtOH=1:99) and stirred for 25 min. at room temperature. The mixture was then neutralized with saturated NaHCO$_3$ aq., extracted with CHCl$_3$ (3×50 mL), and the combined organic layers were dried over Na$_2$SO$_4$, filtered, and concentrated. Flash chromatography (10%→30% EtOAc/hexanes) provided MOM-ether (+)-13 (175.6 mg, 98%) as a colorless oil: [α]$_D^{23}$ +16.0° (c 2.0, CHCl$_3$); IR (CHCl$_3$) 3502 (br), 2960 (s), 2932 (s), 2880 (m), 2856 (m), 1616 (w), 1514 (m), 1456 (m), 1374 (w), 1302 (w), 1250 (s), 1145 (w), 1091 (s), 1038 (s), 956 (m), 905 (w), 835 (s), 772 (m) cm$^{-1}$; $^1$H-NMR (500 MHz, CDCl$_3$) δ 7.27 (d, J=8.7 Hz, 2H), 6.87 (d, J=8.7 Hz, 2H), 6.60 (ddd, J=16.7, 10.7, 10.5 Hz, 1H), 6.03 (apparent t, J=10.9 Hz, 1H), 5.58 (apparent t, J=10.5 Hz, 1H), 5.21 (d, J=16.7 Hz, 1H), 5.12 (d, J=10.3 Hz, 1H), 5.02 (d, J=10.1 Hz, 1H), 4.65 (s, 2H), 4.57 (d, J=10.6 Hz, 1H), 4.46 (d, J=10.6 Hz, 1H), 3.81 (dd, J=10.8, 3.6 Hz, 1H), 3.80 (s, 3H), 3.46 (m, 2H), 3.43 (s, 3H), 3.23 (m, 2H), 3.00 (m, 1H), 2.59 (m, 1H), 2.04 (apparent t, J=12.2 Hz, 1H), 1.79 (m, 3H), 1.71 (apparent d, J=13.2 Hz, 1H), 1.59 (s, 3H), 1.50 (br s, 1H), 1.10 (d, J=6.8 Hz, 3H), 1.01 (d, J=7.1 Hz, 6H), 0.95 (s, 9H), 0.92 (d, J=6.7 Hz, 3H), 0.72 (d, J=6.7 Hz, 3H), 0.10 (s, 3H), 0.09 (s, 3H); $^{13}$C-NMR (125 MHz, CDCl$_3$) δ 159.1, 134.5, 133.3, 132.3, 131.2, 130.1, 129.1, 129.0, 117.5, 113.7, 99.1, 87.6, 84.6, 77.0, 74.9, 65.0, 56.3, 55.3, 40.2, 37.4, 36.2, 35.6, 35.4, 34.8, 26.3, 23.2, 18.7, 18.6, 15.5, 15.2, 14.5, 10.7, −3.3, −3.3; high resolution mass spectrum (FAB, NBA) m/z 669.4520 [(M+Na)$^+$; calcd for C$_{38}$H$_{66}$O$_6$SiNa: 669.4526].

Example 10

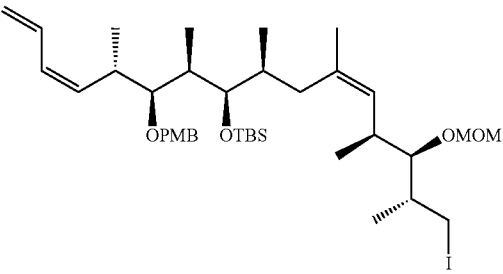

35

Iodide 35. A solution of (+)-13 (47.9 mg, 0.0741 mmol), PPh$_3$ (29.2 mg, 0.111 mmol) and imidazole (7.6 mg, 0.111 mmol) in benzene.Et$_2$O (1:2) (1.06 mL) was cooled to 0° C., and treated with iodine (28.2 mg, 0.111 mmol). The reaction mixture was warmed to room temperature and stirred for 12 min. The reaction was then quenched with saturated NaHCO$_3$ aq. (5 mL). The mixture was extracted with Et$_2$O (3×15 mL), and the combined organics were dried over Na$_2$SO$_4$, filtered, and concentrated. Flash chromatography (15% EtOAc/hexanes) provided a mixture of the desired alkyl iodide 35 and PPh$_3$, which was taken onto the next step without further purification.

Example 11

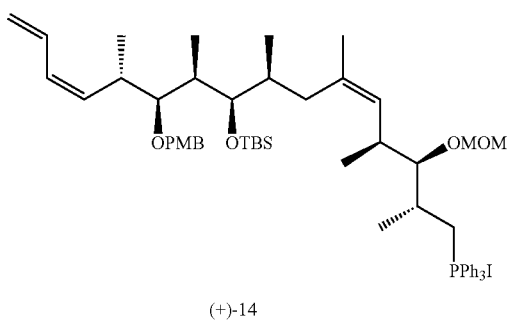

(+)-14

Wittig Salt (+)14. To the neat alkyl iodide 35 (mixed with PPh$_3$) was added additional PPh$_3$ (194 mg, 0.741 mmol) and i-Pr$_2$NEt (0.37 mL) at room temperature under argon. The mixture was warmed to 100° C. and stirred. After 18 h, the reaction mixture was cooled to room temperature and diluted with CH$_2$Cl$_2$ (0.5 mL). The resulting solution was directly purified via flash chromatography (20% EtOAc/hexane, then 15%→50% CH$_3$CN/CH$_2$Cl$_2$) to give Wittig salt (+)-14 as a colorless oil (52.2 mg, 70% for 2 steps) and the mixture of cyclized byproducts (13.1 mg, 28% for 2 steps): Wittig Salt (+)-14: [α]$_D^{23}$ +17.8° (c 1.0, CHCl$_3$); IR (CHCl$_3$) 2962 (s), 2931 (s), 2854 (m), 1612 (w), 1587 (w),1514 (m), 1456 (m), 1438 (w), 1249 (s), 1035 (s), 835 (s), 750 (s) cm$^{-1}$; $^1$H-NMR (500 MHz, CDCl$_3$) δ 7.74 (m, 15H), 7.26 (d, J=8.6 Hz, 2H), 6.86 (d, J=8.6 Hz, 2H), 6.55 (ddd, J=16.8, 10.7, 10.5 Hz, 1H), 5.94 (apparent t, J=11.0 Hz, 1H), 5.53 (apparent t, J=10.5 Hz, 1H), 5.13 (d, J=16.8 Hz, 1H), 5.08 (d, J=10.1 Hz, 1H), 5.05 (d, J=10.1 Hz, 1H), 4.70 (d, J=6.1 Hz, 1H), 4.66 (d, J=6.1 Hz, 1H), 4.55 (d, J=10.5 Hz, 1H), 4.44 (d, J=10.5 Hz, 1H), 3.78 (s, 3H), 3.72 (apparent t, J=16.8 Hz, 1H), 3.42 (dd, J=4.8, 3.5 Hz, 1H), 3.34 (s, 3H), 3.31 (apparent t, J=5.8 Hz, 1H), 3.22 (m, 2H), 2.96 (m, 1H), 2.50 (m, 1H), 2.14 (m, 1H), 1.92 (apparent t, J=12.2 Hz, 1H), 1.73 (m, 2H), 1.59 (m, 1H), 1.50 (s, 3H), 1.09 (d, J=6.9 Hz, 3H), 0.94 (d, J=6.9 Hz, 3H), 0.90 (s, 9H), 0.83 (d, J=6.6 Hz, 3H), 0.76 (d, J=6.8 Hz, 3H), 0.65 (d, J=6.7 Hz, 3H), 0.08 (s, 3H), 0.04 (s, 3H); $^{13}$C-NMR (125 MHz, CDCl$_3$) δ 159.1, 135.3, 135.3, 134.3, 133.8, 133.5, 132.1, 131.0, 130.7, 130.6, 129.1, 128.9, 118.8, 118.1, 117.6, 113.7, 99.3, 88.1, 88.0, 84.5, 75.0, 56.2, 55.3, 54.8, 39.9, 35.7, 35.5, 35.3, 34.2, 31.7, 26.2, 22.9, 18.7, 18.5, 17.9, 15.6, 14.8, 10.7, −3.3, −3.4; high resolution mass spectrum (ES$^+$) m/z 891.5537 [(M−I)$^+$; calcd for C$_{56}$H$_{80}$O$_5$PSi: 891.5513]. Cyclized byproducts; high resolution mass spectrum (ES$^+$) m/z 651.4414 [(M+Na)$^+$; calcd for C$_{38}$H$_{64}$O$_5$SiNa: 651.4421].

Example 12

Comparative Example

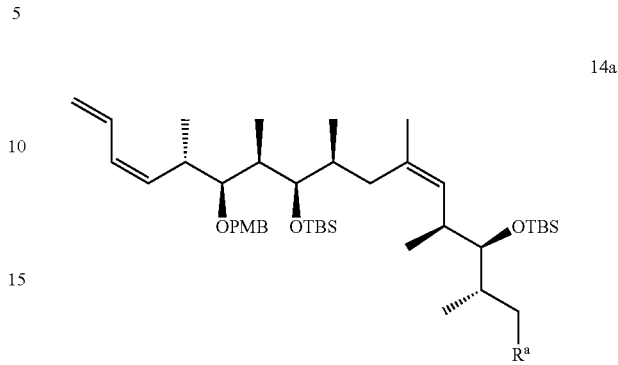

14a

Preparation of Silyl-protected Wittig salt under extremely high pressure conditions. Following the method of Smith, et al. (U.S. Pat. No. 6,242,616 B1 (2001)), phosphonium salt 14a (R$^a$ is P$^+$(Ph)$_3$I$^-$) was prepared. A solution of iodine (1.07 g, 4.24 mmol) in 10 mL of Et$_2$O was added dropwise to a vigorously stirred solution of alcohol (+)-74 (R$^a$ is OH) (1.41 g, 1.97 mmol; 8:1 mix of cis/trans diene isomers), PPh$_3$ (1.37 g, 5.22 mmol) and imidazole (342 mg, 5.02 mmol) in benzene/ether (1:1, 40 mL) at 0° C. The resultant canary yellow suspension was stirred 30 min at 0° C. and poured into 150 mL of 1:1 water/hexanes. The layers were separated and the aqueous layer was extracted with hexanes. The combined organic layers were washed with saturated aqueous sodium metabisulfite (2×50 mL), water (1×50 mL) and brine (100 mL). The clear, colorless organic layer was dried over MgSO$_4$, filtered and concentrated. The resulting white slurry was loaded onto a plug of SiO$_2$ with a minimal amount of CH$_2$Cl$_2$ and rapidly eluted off the column (0.05% Et$_3$N/2% Et$_2$O/hexanes) to afford the corresponding iodide as colorless oil (8:1 ds mixture of diene isomers; contaminated with ca. 20% PPh$_4$) which was taken on to the next step without further purification: $^1$H NMR (500 MHz, C$_6$D$_6$, major diene isomer). 7.51 (m, 6H), 7.43 (d, J=8.6 Hz, 2H), 7.18 (m, 9H), 6.97 (d, J=8.6 Hz, 2H), 6.84 (ddd, J=16.8, 10.8, 10.8 Hz, 1H), 6.23 (apparent t, J=10.8 Hz, 1H), 5.84 (apparent t, J=10.5 Hz, 1H), 5.33 (dd, J=16.8, 1.9 Hz, 1H), 5.27 (d, J=10.4, 1H), 5.23 (d, J=10.2 Hz), 4.74 (d, J=10.7 Hz, 1H), 4.66 (d, J=10.7 Hz, 1H), 3.76 (apparent t, J=4.4 Hz, 1H), 3.58 (dd, J=6.6, 4.0 Hz, 1H), 3.48 (m, 2H), 3.46 (s, 3H), 3.24 (m, 1H), 3.17 (dd, J=9.6, 8.0 Hz, 1H), 2.80 (m, 1H), 2.44 (apparent t, J=12.3 Hz, 1H), 2.17 (m, 1H), 2.10 (m, 1H), 2.02 (m, 1H), 1.78 (s, 3H), 1.38 (d, J=6.9 Hz, 3H), 1.27 (d, J=6.8 Hz, 3H), 1.20 (s, 9H), 1.18 (m, 6H), 1.10 (s, 9H), 1.06 (d, J=6.7 Hz, 3H), 0.33 (s, 3H), 0.31 (s, 3H), 0.24 (s, 3H), 0.23 (s, 3H).

To a solution of above Iodide in benzene/toluene (7:3, 5.0 mL) was added diisopropylethylamine (0.2 mL, 1.14 mmol) and triphenylphosphine (2.5 g, 9.53 mmol). The resulting solution was loaded into a 20 mL polyethylene syringe and capped in such a way as to eliminate any trapped air (3×1.0 mL rinse of 7:3 benzene/toluene solution). The syringe was loaded into a high pressure apparatus and subjected to a pressure of 12.8 Kbar. After 14 days, the reaction mixture was concentrated and chromatographed (gradient elution, 20% EtOAc/hexanes to 50% EtOAc/hexanes, then 20% MeCN/CH$_2$Cl$_2$) to provide 14a as a light yellow solid [1.68 g, 78% yield from alcohol 46; 8:1 dr]: .[]23, D +22° (c 1.0, CHCl3); IR (CHCl3) 2940, 1610, 1580, 1250 cm$^{-1}$; $^1$H NMR (500 MHz, CDCl$_3$, Major isomer). 7.75 (m, 15H) 7.27 (d, J=8.6 Hz, 2H) 6.86 (d, J=8.6 Hz, 2H), 6.54 (ddd, J=16.8, 10.6, 10.6 Hz, 1H), 5.89 (apparent t, J=11.0 Hz, 1H), 5.50 (apparent t, J=10.5 Hz, 1H),5.30 (d, J=10.6 Hz, 1H), 5.12 (d, J=16.8 Hz, 1H), 5.08 (d, J=10.2 Hz, 1H), 4.56 (d, J=10.4 Hz, 1H), 4.45 (d, J=10.4 Hz, 1H), 3.78 (s, 3H), 3.70 (m, 1H), 3.69 (dd, J=6.7, 4.6 Hz, 1H), 3.42 (dd, J=5.3, 3.1 Hz, 1 H), 3.23 (dd, J=7.9, 3.2 Hz, 1H), 3.19 (m, 1H), 2.97 (m, 1H), 2.41 (m, 1H), 2.03 (m, 1H), 1.94 (apparent t, J=12.2 Hz, 1H), 1.84 (m, 2H), 1.57 (m, 1H), 1.54 (s, 3H), 1.10 (d, J=6.8 Hz, 3H), 0.96 (d, J=6.8 Hz, 3H), ).89 (m, 21H), 0.69 (d, J=6.9 Hz, 3H), 0.66 (d, J=6.7 Hz, 3H), 0.095 (s, 3H), 0.08 (s, 3H), 0.04 (s, 3H), −0.05 (s, 3H); 13C NMR (125 MHz, CDCl3). 159.1, 135.3, 135.2, 134.2, 133.5, 133.4, 132.5, 132.3, 131.0, 130.9, 130.7, 130.6, 130.4, 129.1, 128.8, 128.2, 118.6, 118.0, 117.6, 113.7, 84.6, 80.0, 79.9, 76.8, 75.1, 55.3, 39.8, 35.8, 35.5, 35.3, 35.2, 26.2, 26.1 (2), 26.0, 22.6, 18.6, 18.5, 18.2, 17.4, 16.9, 15.0, 10.5, −3.3, −3.4 (2), −4.0; high resolution mass spectrum (FAB, NBA) m/z 961.6134[(M−I)$^+$; calcd for C$_{60}$H$_{90}$O$_4$PSi$_2$: 961.6115].

Example 13

Comparative Example

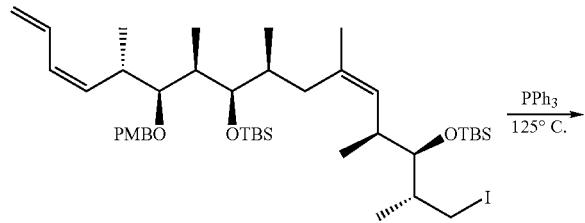

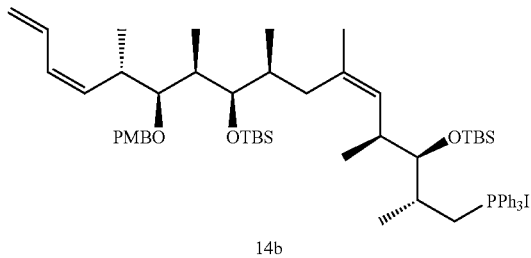

14b

Preparation of Silyl-protected Wittig salt 14b under ambient pressure conditions. To the neat alkyl iodide (0.1 mg, 0.0001 mmol) was added PPh$_3$ (0.5 mg, 0.0019 mmol) at room temperature. The mixture was warmed to 125° C. and stirred for 1 h. The reaction mixture was cooled to room temperature and taken up in CDCl$_3$ (0.5 mL). $^1$H NMR showed a 1:1 mixture of starting material to cyclopentane by-products, with only a trace of product Wittig salt 14b observed.

Example 14

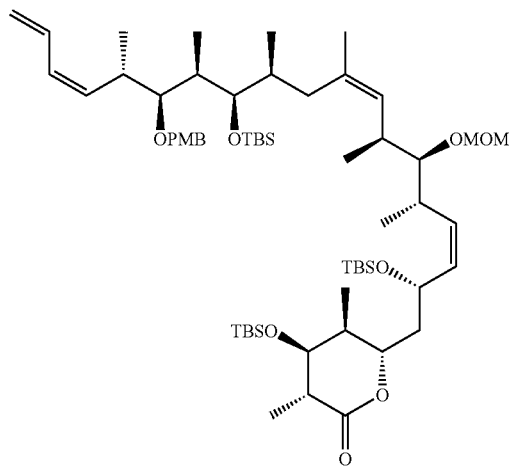

(+)-15

Tetraene (+)-15 (Wittig Coupling). Phosphonium salt (+)-14 (330 mg, 0.324 mmol; 14:1 ratio of diene isomers), was azeotropically dried with benzene (3×0.5 mL) using a double manifold and further dried by heating to 50° C. under vacuum (0.2 torr) for 24 h. The flask was back-filled with argon, dissolved in 1.5 mL of freshly distilled THF and cooled to −78° C. The resultant solution was treated with methyllithium-lithium bromide complex (2.2 M in pentane, 0.147 mL), warmed to 0° C., stirred for 30 min., and then recooled to −78° C. To this orange/red solution was transferred dropwise via syringe a solution of aldehyde (−)-C (128 mg, 0.287 mmol) in THF (1.0 mL+1×0.5 mL rinse) over 45 min. The resulting orange solution was stirred for a further 30 min. at −78° C., and then warmed to −10° C. and allowed to stir for 3 hrs. The resulting light yellow solution was quenched with saturated NH$_4$Cl and diluted (Et$_2$O/H$_2$O). The layers were separated, and the aqueous layer was extracted (3×Et$_2$O). The combined organic layers were dried (MgSO$_4$), concentrated, and chromatographed (gradient elution: 3% EtOAc/hexanes→50% EtOAc/hexanes; then 40% CH$_3$CN/CH$_2$Cl$_2$) to afford cis isomer (+)-15 (164 mg, 48%; clear oil, 14:1 ratio of diene isomers), trans isomer (11.5 mg, 3.4%; clear oil; 14:1 ratio of diene isomers), and phosphonium salt (+)-14 (132 mg, 39%; 14:1 ratio of diene isomers): Cis olefin (+)-15: [α]$_D^{23}$ +32.0° (c 0.3 CHCl$_3$); IR (NaCl) 2958, 2929, 2884, 2857, 1734, 1472, 1253, 1045, 836 cm$^{-1}$; $^1$H-NMR (500 MHz, CDCl$_3$) δ 7.25 (d, J=8.1 Hz, 2H), 6.84 (d, J=8.9 Hz, 2H), 6.57 (ddd, J=17.1, 10.8, 10.8 Hz, 1H), 6.00 (apparent t, J=10.8 Hz, 1H), 5.55 (apparent t, J=10.8 Hz, 1H), 5.31 (dd, J=10.8, 7.8 Hz, 1H), 5.24-5.16 (m, 2H), 5.10 (d, J=10.4 Hz, 1H), 4.99 (d, J=10.0 Hz, 1H), 4.80 (apparent t, J=8.9 Hz, 1H), 4.59 (ABq, J$_{AB}$=6.7 Hz, Δv$_{AB}$=26.4 Hz, 2H), 4.54 (d, J=10.4 Hz, 2H), 4.19 (apparent t, J=10.8 Hz, 1H), 3.77 (s, 3H), 3.61 (apparent t, J=2.6 Hz, 1H), 3.43 (apparent t, J=4.1 Hz, 1H), 3.24 (s, 3H), 3.23 (dd, J=7.4, 3.7 Hz, 1H), 3.04 (apparent t, J=5.6 Hz, 1H), 2.98 (ddd, J=10.0, 6.7, 3.3 Hz, 1H), 2.73-2.65 (m, 1H), 2.60 (ddd, J=15.3, 7.4, 3.0 Hz, 1H), 2.49 (ddd, J=16.8, 13.0, 6.3 Hz, 1H), 2.02 (apparent t, J=12.3 Hz, 1H), 1.85-1.61 (m, 4H), 1.60-1.54 (m, 2H), 1.54 (s, 3H), 1.22 (d, J=7.4 Hz, 3H), 1.08

(d, J=6.7 Hz, 3H), 0.99 (d, J=7.1 Hz, 3H), 0.96-0.91 (m, 6H), 0.93 (s, 9H), 0.90 (d, J=6.7 Hz, 3H), 0.87 (s, 9H), 0.85 (s, 9H), 0.70 (d, J=7.1 Hz, 3H), 0.08 (s, 3H), 0.07 (s, 3H), 0.06 (s, 3H), 0.05 (s, 3H), 0.03 (br s, 6H); $^{13}$C-NMR (125 MHz, CDCl$_3$) δ 173.3, 158.9, 134.4, 133.6, 132.4, 132.1, 131.9, 131.2, 130.8, 129.1, 129.0, 117.6, 113.6, 97.4, 86.3, 84.5, 77.0, 74.9, 74.69, 74.68, 64.6, 55.9, 55.2, 43.9, 42.3, 40.1, 36.2, 35.5, 35.3 (2), 34.2, 34.1, 26.2, 25.8, 25.6, 23.0, 18.6, 18.5, 18.0, 17.8, 16.63, 16.61, 16.2, 14.7, 13.9, 10.5, −3.29, −3.32, −4.4, −4.6, −4.9 (2); high resolution mass spectrum (ES+) m/z 1079.7214 [(M+Na)$^+$; calcd for C$_6$OH$_{108}$O$_9$Si$_3$Na: 1079.7199].

Example 15

Comparative Example

Preparation of C-11 Q-protected Δ8,9-Double bond Compound under "Smith" conditions. U.S. Pat. No. 6,242,616 B1 (2001). Tetraene (+)-15 (Wittig Coupling): Wittig salt 14 (75 mg, 0.074 mmol; 12:1 ratio of diene isomers), was azeotropically dried with benzene (3×0.5 mL) using a double manifold and further dried by heating to 50° C. under vacuum (0.2 torr) for 24 h. The flask was back-filled with argon, dissolved in 1 mL of freshly distilled THF, sparged with argon for 15 min, and cooled to −30° C. The resultant solution was treated with methyllithium-lithium bromide complex (2.2 M in pentane, 0.033 mL) and stirred 1 hour. To this orange/red solution was transferred via cannula a degassed solution of aldehyde (−)-C (40 mg, 0.089 mmol) in THF (0.5 mL+1×0.5 mL rinse) over 3 min. The orange solution was stirred at −30° C. over 3.25 h. The resulting light yellow solution was quenched with saturated NH$_4$Cl and diluted (Et2O/H$_2$O). The layers were separated, and the aqueous layer was extracted (3×Et$_2$O). The combined organic layers were dried (MgSO$_4$), concentrated, and chromatographed (gradient elution: 2% EtOAc/hexanes→50% EtOAc/hexanes; then 40% CH$_3$CN/CH$_2$Cl$_2$) to afford cis isomer 15 (37.5 mg, 48%; clear oil, 12:1 ratio of diene isomers), trans isomer (10 mg, 13%; clear oil; 12:1 ratio of diene isomers), and phosphonium salt (+)-13 (20 mg, 27%; 12:1 ratio of diene isomers):

Cis olefin 15: [α]$_D^{23}$ +32.00 (c 0.3 CHCl$_3$); IR (NaCl) 2958, 2929, 2884, 2857, 1734, 1472, 1253, 1045, 836 cm$^{-1}$; $^1$H NMR (500 MHz, CDCl$_3$, major diastereomer) δ 7.25 (d, J=8.1 Hz, 2 H), 6.84 (d, J=8.9 Hz, 2H), 6.57 (ddd, J=17.1, 10.8, 10.8 Hz, 1 H), 6.00 (apparent t, J=10.8 Hz, 1 H), 5.55 (apparent t, J=10.8 Hz, 1H), 5.31 (dd, J=10.8, 7.8 Hz, 1H), 5.24-5.16 (m, 2H), 5.10 (d, J=10.4 Hz, 1H), 4.99 (d, J=10.0 Hz, 1H), 4.80 (apparent t, J=8.9 Hz, 1H), 4.59 (ABq, J$_{AB}$=6.7 Hz, Δv$_{AB}$=26.4 Hz, 2 H), 4.54 (d, J=10.4 Hz, 2H), 4.19 (apparent t, J=10.8 Hz, 1H), 4.44 (d, J=10.4 Hz, 2H), 3.77 (s, 3H), 3.61 (apparent t, J=2.6 Hz, 1H), 3.43 (apparent t, J=4.1, 4.1 Hz, 1H), 3.24 (s, 3H), 3.23 (dd, J=7.4, 3.7 Hz, 1H), 3.04 (apparent t, J=5.6 Hz, 1H), 2.98 (ddd, J=10.0, 6.7, 3.3 Hz, 1H), 2.73-2.65 (m, 1H), 2.60 (ddd, J=15.3, 7.4, 3.0 Hz, 1H), 2.49 (ddd, J=16.8, 13.0, 6.3 Hz, 1H), 2.02 (apparent t, J=12.3 Hz, 1H), 1.85-1.61 (m, 5H), 1.60-1.54 (m, 2H), 1.54 (s, 3H), 1.22 (d, J=7.4 Hz, 3H), 1.08 (d, J=6.7 Hz, 3H), 0.99 (d, J=7.1 Hz, 3H), 0.96-0.91 (m, 6H), 0.93 (s, 9H), 0.90 (d, J=6.7 Hz, 3H), 0.87 (s, 9H), 0.85 (s, 9H), 0.85 (s, 9H), 0.70 (d, J=7.1 Hz, 3H), 0.08 (s, 3H), 0.07 (s, 3H), 0.051 (s, 3H), 0.06 (s, 3H), 0.05 (s, 3H), 0.03 (br s, 6H); high resolution mass spectrum (ES$^+$) m/z, 1079.7214 [(M+Na)$^+$; calcd for C$_{60}$H$_{108}$O$_9$Si$_3$Na: 1079.7199].

Example 16

Comparative Example

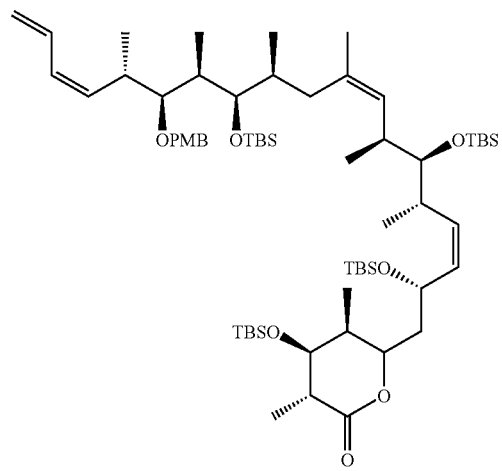

15a

Preparation of C-11 Bulky Silyl-protected Δ$^{8,9}$-Double bond Compound under "Smith" conditions. Following the method of Smith, et al. (U.S. Pat. No. 6,242,616 B1 (2001)), Tetraene 15a (Wittig Coupling): Phosphonium salt 14a (1.20 g, 1.10 mmol; 8:1 ratio of diene isomers), was azeotropically dried with benzene (3×1.5 mL) using a double manifold and further dried by heating to 50° C. under vacuum (0.2 torr) for 12 h. The salt was dissolved in 6 mL of freshly distilled THF, sparged with argon for 15 min, and cooled to −20° C. The resultant solution was treated with sodium bis(trimethylsilyl)amide (1.0 M in THF, 1.04 mL), stirred 15 min, warmed to 0° C., stirred 30 min, and re-chilled to −24° C. To this orange/red solution was transferred via cannula a degassed solution of aldehyde (−)-C (508 mg, 1.14 mmol) in THF (3 mL+1×0.5 mL rinse) over 7 min. The orange solution was allowed to slowly warm to −8° C. over 3.25 h. The resulting light yellow solution was quenched with saturated NH$_4$Cl, diluted with Et$_2$O and H$_2$O. The layers were separated, and the aqueous layer was extracted (3×Et$_2$O). The combined organic layers were dried (Na$_2$SO$_4$), concentrated, and chromatographed (gradient elution; 2% EtOAc/hexanes or 50% to EtOAc/hexanes; then 40% CH$_3$CN/CH$_2$Cl$_2$) to afford cis isomer 58 (767 mg, 65%; white foam, 8:1 ratio of diene isomers), trans isomer 58 (50 mg, 4%; clear oil; 8:1 ratio of diene isomers), and phosphonium salt 75 (399 mg, 33%; 8:1 ratio of diene isomers). [enant-(+)-58 [α]$_D^{23}$ −32° (c 0.23, CHCl$_3$)]; IR (CHCl$_3$) 1725 cm$^{-1}$; $^1$H NMR (500 MHz, CDCl$_3$, major diene isomer) δ 7.25 (d, J=9.0 Hz, 2H), 6.84 (d, J=8.7 Hz, 2H), 6.57 (ddd, J=16.7, 10.6, 10.6 Hz, 1H), 6.00 (apparent t, J=11.0 Hz, 1H), 5.55 (apparent t, J=10.5 Hz, 1H), 5.26 (dd, J=11.1, 7.9 Hz, 1H), 5.19 (dd, J=15.4, 1.4 Hz, 1H), 5.18 (apparent t, J=10.1 Hz, 1H), 5.10 (d, J=10.2 Hz, 1H), 5.01 (d, J=10.0 Hz, 1H), 4.75 (apparent t, J=9.2 Hz, 1H), 4.50 (ddd, J=10.5, 1.3, 1.3 Hz, 1H), 4.50 (ABq, J$_{AB}$=10.6 Hz, Δ$_{AB}$=42.6 Hz, 2H), 3.78 (s, 3H), 3.60 (apparent t, J=2.4 Hz, 1H), 3.42 (dd, J=5.1, 3.7 Hz, 1H), 3.23 (dd, J=7.5, 3.7 Hz, 1H), 3.20 (apparent t, J=5.4 Hz, 1H), 3.01-2.94 (m, 1H), 2.60 (qd, J=7.7, 2.6 Hz, 1H), 2.62-2.55 (m, 1H), 2.45-2.38 (m, 1H), 1.98 (apparent t, J=12.3 Hz, 1H), 1.84-1.67 (m, 3H), 1.63 (br d, J=13.2 Hz, 1H), 1.52 (s, 3H), 1.55-1.48 (m, 1H), 1.20 (d, J=7.6 Hz, 3H), 1.09 (d, J=6.8 Hz, 3H), 0.98 (d, J=6.8 Hz, 3H), 0.93 (apparent d, J=6.7 Hz, 6H), 0.93 (s, 9H), 0.89 (s, 9H), 0.86 (s, 9H), 0.85 (s, 9H), 0.84 (d, J=6.8 Hz, 3H), 0.69 (d, J=6.7 Hz, 3H), 0.085 (s, 3H), 0.079 (s, 3H), 0.051 (s, 3H), 0.046 (s, 3H), 0.042 (s, 3H), 0.029 (s, 3H), 0.028 (s, 3H), −0.02 (s, 3H); $^{13}$C NMR (125 MHz, CDCl$_3$) δ 173.2, 159.1, 134.4, 133.4, 132.4, 132.2, 131.9, 131.3, 131.2, 129.11, 129.09, 117.6, 113.7, 84.6, 80.5, 76.9, 75.0, 74.9, 64.6, 55.3, 44.1, 42.7, 40.1, 37.5, 36.0, 35.44, 35.37, 35.2, 34.2, 26.31, 26.28, 25.9, 25.7, 23.0, 18.7, 18.6, 18.4, 18.1, 18.0, 17.1, 16.5, 16.4, 14.9, 14.1, 10.5, −3.0, −3.2, −3.3, −4.3, −4.4, −4.5, −4.8, −4.9; high resolution mass spectrum (FAB, NBA) m/z 1149.7836 [(M+Na)$^+$; calcd for C$_{64}$H$_{118}$O$_8$Si$_4$Na: 1149.7802].

Example 17

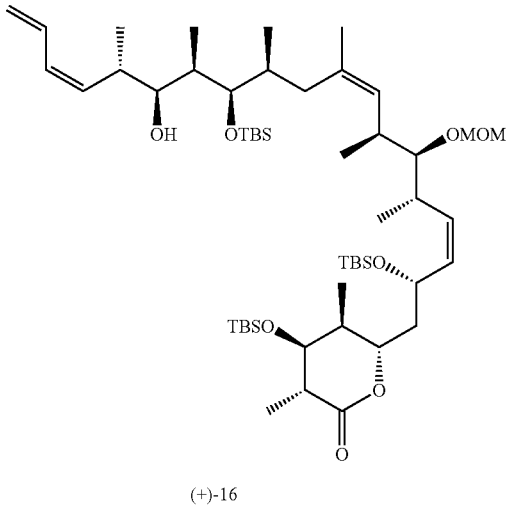

(+)-16

Alcohol (+)-16. At 0° C., a solution of PMB ether (+)-15 (124 mg, 0.117 mmol, 14:1 mixture of cis/trans diene isomers) in CH$_2$Cl$_2$ (6 mL) was treated with H$_2$O (100 μL) and DDQ (40 mg, 0.160 mmol). The mixture was stirred for 50 min. at 0° C., warmed to rt and stirred an additional 15 min. The mixture was quenched with 7.0 mL saturated NaHCO$_3$, and diluted with CH$_2$Cl$_2$ (25 mL) and H$_2$O (30 mL). The layers were separated and the aqueous layer was extracted with 3×25 mL CH$_2$Cl$_2$. The combined organic layers were washed with brine (10 mL), dried (MgSO$_4$), filtered, and concentrated. Flash chromatography (gradient elution; 5% EtOAc→20% EtOAc/hexanes) provided (+)-16 (101 mg, 92%) as a colorless oil: [α]$_D^{23}$ +35.6° (c 1.0, CDCl$_3$)]; IR (NaCl) 3510, 2957, 2929, 2884, 2857, 1734, 1472, 1252, 1097, 1044 cm$^{-1}$; $^1$H-NMR (500 MHz, CDCl$_3$) δ 6.61 (ddd, J=17.1, 10.9, 10.8 Hz, 1H), 6.12 (apparent t, J=11.1 Hz, 1H), 5.34-5.28 (m, 2H), 5.25-5.19 (m, 1H), 5.23 (d, J=10.1 Hz, 1H), 5.13 (d, J=10.1 Hz, 1H), 5.02 (d, J=10.1 Hz, 1H), 4.80 (apparent t, J=8.6 Hz, 1H), 4.59 (ABq, J$_{AB}$=6.7 Hz, Δv$_{AB}$=18.9 Hz, 2H), 4.49, (apparent t, J=10.1 Hz, 1H), 3.63 (apparent t, J=2.6 Hz, 1H), 3.60 (dd, J=5.6, 3.4 Hz, 1H), 3.34 (s, 3H), 3.34-3.30 (m, 1H), 3.08 (apparent t, J=5.6 Hz, 1H), 2.79 (ddd, J=16.7, 14.1, 6.7 Hz, 1H), 2.69 (ddd, J=16.0, 12.6, 6.3 Hz, 1H), 2.60 (ddd, J=14.9, 7.4, 2.6 Hz, 1H), 2.54 (ddd, J=16.4, 12.6, 6.3 Hz, 1H), 2.18 (apparent t, J=12.3 Hz, 1H), 1.90-1.75 (m, 4H), 1.73-1.69 (m, 2H), 1.59 (s, 3H), 1.55 (m, 1H), 1.22 (d, J=7.4 Hz, 3H), 0.97-0.92 (m, 15H), 0.91 (s, 9H), 0.87 (s, 9H), 0.85 (s, 9H), 0.74 (d, J=6.7 Hz, 3H), 0.07 (apparent s, 6H), 0.06 (s, 3H), 0.05 (s, 3H), 0.04 (s, 3H), 0.03 (s, 3H); $^{13}$C-NMR (125 MHz, CDCl$_3$) δ 173.4, 134.6, 133.7, 132.3, 132.0, 131.9, 130.9, 130.7, 118.3, 97.5, 86.3, 78.9, 77.0, 76.2, 74.7, 64.7, 55.9, 43.9, 42.3, 38.0, 36.5, 36.3, 35.5, 34.9, 34.3, 34.2, 26.2, 25.8, 25.7, 23.24, 18.4, 18.0, 17.9, 17.1, 16.8, 16.5, 16.2, 13.9, 13.6, 9.4, −3.3, −3.8, −4.4, −4.6, −4.9 (2); high resolution mass spectrum (ES$^+$) m/z 959.6625 [(M+Na)$^+$; calcd for C$_{52}$H$_{100}$O$_8$Si$_3$Na: 959.6624].

Example 18

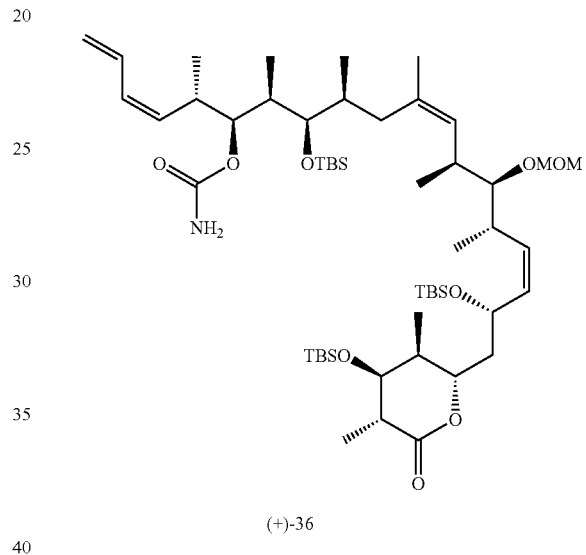

(+)-36

Carbamate (+)-36. A solution of alcohol (+)-16 (10 mg, 0.011 mmol) in CH$_2$Cl$_2$ (1.0 mL) was treated with a 1 M solution of Cl$_3$CCON=C=O in toluene (16 μL, 0.016 mmol) at room temperature for 30 min. Neutral Al$_2$O$_3$ (1 g) was added, followed by 2 mL CH$_2$Cl$_2$. After 4 h, the material was transferred to a cotton-plugged chromatography column and flushed from the Al$_2$O$_3$ (EtOAc, 50 mL). Concentration and purification by preparatory TLC (250 μm plate, 20% ethyl acetate/hexanes) provided 6.0 mg (+)-36 (60%) as a colorless oil and 3.5 mg (35%) of recovered (+)-16. Carbamate (+)-36: [α]$_D^{23}$ +46.20 (c 0.5, CHCl$_3$); IR (NaCl) 3510, 3360, 2957, 2936, 2884, 2849, 1732, 1594, 1253, 1033 cm$^{-1}$; $^1$H-NMR (500 MHz, CDCl$_3$) δ 6.58 (ddd, J=17.1, 10.8, 10.8 Hz, 1H), 6.01 (apparent t, J=11.1 Hz, 1H), 5.35 (apparent t, J=10.4 Hz, 1H), 5.33-5.27 (m, 1H), 5.25-5.18 (m, 2H), 5.12 (d, J=10.0 Hz, 1H), 5.01 (d, J=10.0 Hz, 1H), 4.80 (apparent t, J=8.9 Hz, 1H), 4.71 (apparent t, J=6.0 Hz, 1H), 4.60 (ABq, J$_{AB}$=6.7 Hz, Δv$_{AB}$=26.4 Hz, 2H), 4.50 (apparent t, J=10.4 Hz, 1H), 4.44 (br s, 2H), 3.64 (apparent t, J=2.4 Hz, 1H), 3.43 (apparent t, J=4.1 Hz, 1H), 3.34 (s, 3H), 3.06 (apparent t, J=5.6 Hz, 1H), 3.02-2.94 (m, 1H), 2.75-2.66 (m, 1H), 2.65-2.57 (m, 1H), 2.57-2.47 (m, 1H), 2.12 (apparent t, J=12.4 Hz, 1H), 1.93-1.79 (m, 3H), 1.74-1.66 (m, 2H), 1.58 (apparent s, 3H), 1.55-1.50 (m, 1H), 1.23 (d, J=7.4 Hz, 3H), 0.98 (d, J=7.4 Hz, 3H), 0.96 (d, J=6.7 Hz, 3H), 0.94 (d, J=5.4 Hz, 3H), 0.94-0.92 (m, 6H), 0.91 (s, 9H), 0.87 (s, 9H), 0.85 (s, 9H), 0.71 (d, J=6.7 Hz, 3H), 0.08 (s, 3H), 0.06 (apparent s, 9H), 0.04 (s, 3H), 0.03 (s, 3H); $^{13}$C-NMR (125 MHz, MeOH -d6) δ 174.9, 158.7, 133.5, 132.9, 131.9, 131.8, 131.6, 130.5, 129.5, 117.1, 97.3, 86.5, 77.8, 76.7, 74.4, 64.5, 55.0, 44.3, 42.0, 38.4, 36.4, 35.6, 34.9, 34.3, 34.2, 33.4, 25.4, 24.9, 18.0, 17.5, 17.4, 16.6, 16.1, 15.7, 15.2, 13.2, 13.1, 9.3, −4.4, −4.5, −5.4, −5.9 (2), −6.2; high resolution mass spectrum (ES+) m/z 1002.6638 [(M+Na)$^+$; calcd for $C_{53}H_{101}NO_9Si_3Na$: 1002.6682].

Example 19

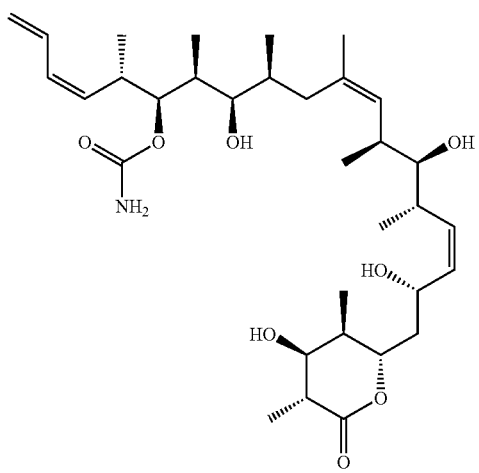

(+)-Discodermolide (+)-Discodermolide (1). Carbamate (+)-36 (6.0 mg, 0.006 mmol) was dissolved in MeOH (1.5 mL) and stirred for 15 min. at room temperature. Aqueous hydrochloric acid (4 N, 1.5 mL) was added in small portions over 4 hours at a rate which minimized precipitation (ca. 10 to 15 min. intervals). After 4 h, an additional 1 mL of 4 N aq HCl was added in one portion, and the resulting solution was stirred for 2 h at rt, diluted with 10 mL of water and poured into 15 mL of EtOAc. The resulting mixture was quenched via careful portionwise addition of NaHCO3 until CO2 evolution ceased. The layers were separated, the aqueous layer was saturated with NaCl and extracted (3×EtOAc). The combined organic layers were washed with brine (1×10 mL), dried (MgSO4), filtered, and concentrated. Flash chromatography using washed SiO2 (10% MeOH/CH2Cl2 then 55% EtOAc/hexanes) via gradient elution (55% EtOAc/hexanes then 10% MeOH/CH2Cl2) provided (+)-discodermolide (3.1 mg, 87% yield) as a white amorphous solid, whose spectral data (1H-NMR, HRMS) matched that previously reported for the natural product.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:
1. A process for preparing a compound of formula I:

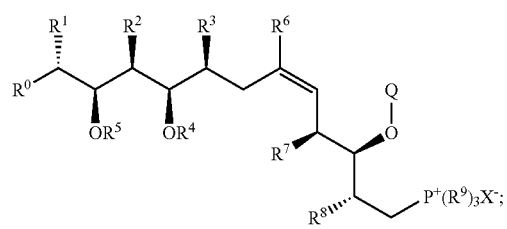

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;
$R^1$, $R^2$, $R^3$, $R^6$, $R^7$ and $R^8$ are independently H or $C_{1-10}$ alkyl;
$R^4$ is an acid labile hydroxyl protecting group;
$R^5$ is an oxidatively labile hydroxyl protecting group;
each $R^9$ is independently $C_{6-14}$ aryl;
Q is H or an acid labile hydroxyl protecting group wherein the hydroxyl protecting group has a mass of 135 Daltons or less and is unbranched at the atom bonded to the oxygen of the hydroxyl group being protected; and
X is halogen;
comprising contacting a compound of formula II:

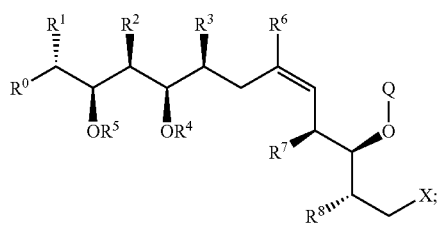

wherein:
$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;
$R^1$, $R^2$, $R^3$, $R^6$, $R^7$ and $R^8$ are independently H or $C_{1-10}$ alkyl;
$R^4$ is an acid labile hydroxyl protecting group;
$R^5$ is an oxidatively labile hydroxyl protecting group;
Q is H or an acid labile hydroxyl protecting group wherein the hydroxyl protecting group has a mass of 135 Daltons or less and is unbranched at the atom bonded to the oxygen of the hydroxyl group being protected; and
X is halogen;
at a pressure of less than about 10,000 psi with a phosphine of formula $P(R^9)_3$ wherein each $R^9$ is independently $C_{6-14}$ aryl;
for a time and under conditions sufficient to prepare the compound of formula I.

2. A process according to claim 1 wherein Q is methoxymethyl, methylthiomethyl, 2-methoxyethoxymethyl, acetyl, benzyloxymethyl, 2-(trimethylsilyl)ethoxymethyl or allyl.

3. A process according to claim 2 wherein Q is methoxymethyl.

4. A process according to claim 1 wherein the X moiety of the compound of formula II is iodo.

5. A process according to claim 1 further comprising a base.

6. A process according to claim 5 wherein the base is non-nucleophilic.

7. A process according to claim 6 wherein the base is isopropyldiethylamine.

8. A process according to claim 1 wherein the reaction is carried out at essentially atmospheric pressure.

9. A process according to claim 1 wherein $R^0$ is alkenyl.

10. A process according to claim 9 wherein $R^0$ is:

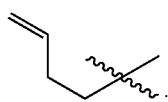

11. A process according to claim 1 wherein $R^1$, $R^2$, $R^3$, $R^6$, $R^7$ and $R^8$ are independently H or $C_{1-3}$ alkyl.

12. A process according to claim 1 wherein $R^1$, $R^2$, $R^7$ and $R^8$ are methyl and $R^3$ and $R^6$ are each independently H or methyl.

13. A process according to claim 1 wherein $R^1$, $R^2$, $R^3$, $R^6$, $R^7$ and $R^8$ are methyl.

14. A process according to claim 1 wherein $R^1$, $R^2$, $R^3$, $R^7$ and $R^8$ are methyl and $R^6$ is H.

15. A process according to claim 1 wherein the reaction temperature is in the range of about 0 to about 200° C.

16. A process according to claim 15 wherein the reaction temperature is in the range of about 20 to about 140° C.

17. A process according to claim 1 wherein the reaction pressure is in the range from about ambient to about 10,000 psi.

18. A process according to claim 17 wherein the reaction pressure is essentially ambient.

19. A process according to claim 1 wherein at least one of $R^9$ is phenyl.

20. A process according to claim 1 wherein $R^5$ is para-methoxybenzyl.

21. A process according to claim 1 wherein $R^4$ is $(R^{16})_3$Si-, and wherein each $R^{16}$ is independently $C_{1-6}$ alkyl.

22. A process according to claim 21 wherein $R^4$ is tert-butyldimethylsilyl.

23. A compound of the formula I:

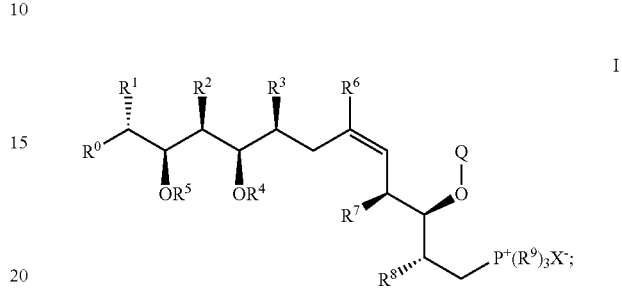

wherein:

$R^0$ is $C_{1-6}$ alkyl, $C_{2-6}$ alkenyl, $C_{2-6}$ alkynyl, $(CH_2)_r(C_{3-6}$ cycloalkyl), $(CH_2)_r$(aryl) or $(CH_2)_r$(heterocycle), wherein r is selected from 0, 1, 2, 3, and 4;

$R^1$, $R^2$, $R^3$, $R^6$, $R^7$ and $R^8$ are independently H or $C_{1-10}$ alkyl;

$R^4$ is an acid labile hydroxyl protecting group;

$R^5$ is an oxidatively labile hydroxyl protecting group;

each $R^9$ is independently $C_{6-14}$ aryl;

Q is H or an acid labile hydroxyl protecting group wherein the hydroxyl protecting group has a mass of 135 Daltons or less and is unbranched at the atom bonded to the oxygen of the hydroxyl group being protected; and X is halogen.

* * * * *